(12) United States Patent
Adamson et al.

(10) Patent No.: US 9,828,404 B2
(45) Date of Patent: Nov. 28, 2017

(54) CROSSLINKED POLYMERIC SUBSTRATES METHODS OF PREPARATION AND END USE APPLICATIONS OF THE SUBSTRATES

(76) Inventors: Douglas H. Adamson, Skillman, NJ (US); Warde T. Collins, Midland, MI (US); David E. Grahan, Long Valley, NJ (US); Robert M. Minnini, Oriental, NC (US)

( * ) Notice: Subject to any disclaimer, the term of this patent is extended or adjusted under 35 U.S.C. 154(b) by 2723 days.

(21) Appl. No.: 12/151,242

(22) Filed: May 5, 2008

(65) Prior Publication Data

US 2009/0274634 A1 Nov. 5, 2009

(51) Int. Cl.

| | | |
|---|---|---|
| *B32B 27/00* | (2006.01) | |
| *A61K 8/72* | (2006.01) | |
| *C08L 83/00* | (2006.01) | |
| *C07H 1/00* | (2006.01) | |
| *A23C 1/00* | (2006.01) | |
| *A23C 9/12* | (2006.01) | |
| *A61Q 11/00* | (2006.01) | |
| *A61Q 15/00* | (2006.01) | |
| *A61Q 17/04* | (2006.01) | |
| *A61Q 19/00* | (2006.01) | |
| *B01D 15/00* | (2006.01) | |
| *B01D 15/08* | (2006.01) | |
| *B01J 20/286* | (2006.01) | |
| *B01J 20/32* | (2006.01) | |
| *B01J 39/26* | (2006.01) | |
| *B01J 41/12* | (2017.01) | |
| *B01J 41/20* | (2006.01) | |
| *C07K 1/22* | (2006.01) | |
| *C11D 3/37* | (2006.01) | |
| *B01J 20/28* | (2006.01) | |
| *B01J 20/10* | (2006.01) | |
| *B82Y 30/00* | (2011.01) | |
| *B01J 39/17* | (2017.01) | |
| *C02F 1/00* | (2006.01) | |
| *C02F 1/28* | (2006.01) | |
| *C02F 1/42* | (2006.01) | |
| *C02F 101/00* | (2006.01) | |
| *C02F 101/20* | (2006.01) | |

(52) U.S. Cl.
CPC ................ *C07H 1/00* (2013.01); *A23C 1/00* (2013.01); *A23C 9/1216* (2013.01); *A61K 8/72* (2013.01); *A61Q 11/00* (2013.01); *A61Q 15/00* (2013.01); *A61Q 17/04* (2013.01); *A61Q 19/00* (2013.01); *B01D 15/00* (2013.01); *B01D 15/08* (2013.01); *B01J 20/103* (2013.01); *B01J 20/286* (2013.01); *B01J 20/28007* (2013.01); *B01J 20/28057* (2013.01); *B01J 20/3204* (2013.01); *B01J 20/327* (2013.01); *B01J 20/3219* (2013.01); *B01J 20/3242* (2013.01); *B01J 20/3263* (2013.01); *B01J 20/3272* (2013.01); *B01J 20/3276* (2013.01); *B01J 20/3278* (2013.01); *B01J 20/3282* (2013.01); *B01J 39/17* (2017.01); *B01J 39/26* (2013.01); *B01J 41/12* (2013.01); *B01J 41/20* (2013.01); *B82Y 30/00* (2013.01); *C07K 1/22* (2013.01); *C11D 3/373* (2013.01); *B01J 2220/54* (2013.01); *B01J 2220/56* (2013.01); *B01J 2220/58* (2013.01); *C02F 1/001* (2013.01); *C02F 1/285* (2013.01); *C02F 1/42* (2013.01); *C02F 2101/006* (2013.01); *C02F 2101/20* (2013.01); *Y10T 428/31663* (2015.04); *Y10T 428/31895* (2015.04); *Y10T 442/2861* (2015.04)

(58) Field of Classification Search
USPC ....... 523/200, 211; 528/12, 28; 502/407, 509
See application file for complete search history.

(56) References Cited

U.S. PATENT DOCUMENTS

| | | | | |
|---|---|---|---|---|
| 4,239,668 | A | * 12/1980 | Clark et al. | .................... 524/262 |
| 4,985,477 | A | *  1/1991 | Collins et al. | ................. 523/212 |
| 5,137,627 | A | *  8/1992 | Feibush | ..................... 210/198.2 |
| 5,695,882 | A |   12/1997 | Rosenberg | |
| 5,997,748 | A |   12/1999 | Rosenberg et al. | |
| 6,160,067 | A | * 12/2000 | Eriyama et al. | .............. 526/279 |
| 6,803,106 | B2 |  10/2004 | Campbell et al. | |

FOREIGN PATENT DOCUMENTS

JP            03024455  A  *  2/1991

\* cited by examiner

*Primary Examiner* — Tae H Yoon
(74) *Attorney, Agent, or Firm* — McKellar IP Law, PLLC

(57) ABSTRACT

A composition of matter wherein the composition comprises a siliceous substrate having silanols on the surface and a polymer selected from the group consisting essentially of a water soluble polymer, a water soluble copolymer, an alcohol soluble polymer, an alcohol soluble copolymer, and combinations of such polymers, wherein the polymer is chemically bonded to the siliceous substrate by a silane linking material having the general formula $O_{3/2}SiQY$ that is derived from an alkoxy-functional silane having the general formula $(RO)_3SiQX$ and processes for preparing the crosslinked polymer that is chemically bonded to the surface of the siliceous substrate.

14 Claims, 15 Drawing Sheets

|  | Primary Metal Cations | | | | |
| --- | --- | --- | --- | --- | --- |
|  | Cu | Hg | Fe | Pb | Ag |
| Cu | – | X | XX | XX | XXX |
| Hg | ≈ | – | X | XX | XX |
| Fe | √ | √ | – | X | XX |
| Pb | √√ | √√ | √ | – | X |
| Ag | √√√ | √√√ | √√ | √ | – |

FIG.14

CROSSLINKED POLYMERIC SUBSTRATES METHODS OF PREPARATION AND END USE APPLICATIONS OF THE SUBSTRATES

BACKGROUND OF THE INVENTION

Since the late 1940's, there has been an increased activity with regard to providing means and methods to clean contaminants from water, especially lakes, ground water, streams and ponds. In addition to the need to clean rivers and streams, there is a great need for having the capability for cleaning waste ponds that are used for detritus from chemical or electrical processes, for example, the removal of radium from quench ponds and the removal of mercury and other metals from conditioned water from manufacturing sites.

A major problem associated with such "cleaning" methods is the ultimate cost. That is why many methods have evolved that use complexing agents and the like rather than fillers as filtration media, as some of these complexing agents are capable of being reversed, that is, after the metal, for example, is sequestered, the process can be reversed to collect the sequestered metal and either reuse it or concentrate it to provide a proper disposal means for it.

Campbell, et al in U.S. Pat. No. 6,803,106 describes a modern material that is used for purification of waste chemical and metal process streams and for the separation and identification of proteins, peptides, and oligionucleotides. This material is a multi-layered macromolecule wherein the layers are covalently bonded together and wherein the macromolecules are covalently bonded to solid particulate substrates.

There is also a system for extracting soluble heavy metals from liquid solutions that is embodied in two patents that issued to Rosenberg and Rosenberg and Pang, respectively. The first is U.S. Pat. No. 5,695,882 that issued Dec. 9, 1997 and the second is U.S. Pat. No. 5,997,748 that issued on Dec. 7, 1999. Both of these patents deal with a process for removing ions of dissolved heavy metals and complex heavy metals from various solutions using an activated surface that is the reaction product of a polyamine with a covalently anchored trifunctional hydrocarbylsilyl that yields non-crosslinked amino groups to which functional chelator groups can be covalently attached.

It is important to note that these materials are non-crosslinked as is expressly set forth by the patentees therein.

BRIEF DESCRIPTION OF THE DRAWINGS

FIG. 14 shows the displacement factors associated with the various metals when using a grafted polymer of this invention, namely, 10 weight % on 250 micron silica.

THE INVENTION

Figure 1:
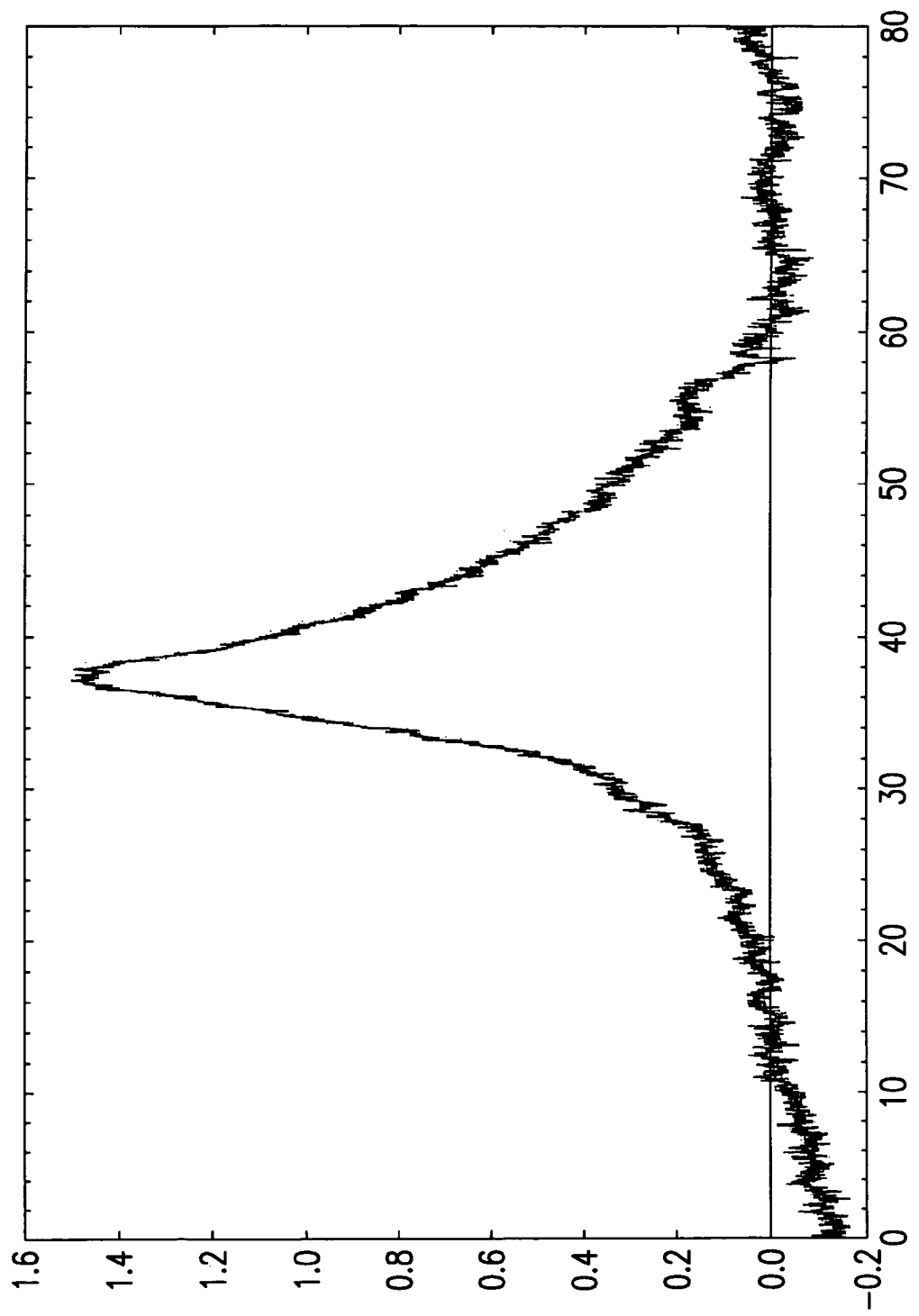
FIG. 1 is a GPC analysis of a 25,000 molecular weight polyethyleneimine polymer that is not grafted to any substrate and is soluble in the reaction water phase.

Thus, what is disclosed and claimed herein in one embodiment is a composition of matter wherein the composition comprises a siliceous substrate having silanols on the surface; a polymer selected from the group consisting essentially of a water soluble polymer, a water soluble copolymer, an alcohol soluble polymer, an alcohol soluble copolymer, and combinations of such polymers.

The polymer is chemically bonded to the siliceous substrate by a silane linking material having the general formula $$O_{3/2}SiQY$$

that is derived from an alkoxy-functional silane. The silane has the general formula $$(RO)_3SiQX$$

wherein R is a hydrocarbon group having from 1 to 6 carbon atoms, Q in each case is a hydrocarbon group having from 0 to 6 carbon atoms, X is a functional group selected from the group consisting of epoxy, halogen, methacrylate, vinyl, amine, allyl, phosphonate, styrlamine, and sulfide, and Y is a residue from a functional group selected from the group consisting of epoxy, halogen, methacrylate, vinyl, amine, allyl, phosphonate, styrlamine, and sulfide.

The incipient amount of the silane is 0.1 to 25 weight percent and the incipient amount of the polymer is 0.1 to 50 weight percent, both based on the weight of the siliceous substrate. Any excess silane is reacted with the reactive groups on the polymer that are not utilized to chemically bond the polymer with the siliceous substrate, the polymer thereby being crosslinked on or near the surface of the polymer.

In another embodiment, there is a process for preparing a crosslinked polymer that is chemically bonded to the surface of a siliceous substrate. The process comprises heating a predetermined amount of water in a reaction vessel with stirring. Thereafter, adding a predetermined amount of a hydrolysis catalyst that is an organic acid, the organic acid having from 1 to 7 carbon atoms.

Thereafter there is added a predetermined amount of a siliceous substrate having reactive silanols and then adding a predetermined amount of silane coupling agent to provide a silane linking material. The silane is an alkoxy-functional silane having the general formula $$(RO)_3SiQX$$

wherein R is a hydrocarbon group having from 1 to 6 carbon atoms, Q is a hydrocarbon group having from 0 to 6 carbon atoms, and X is a functional group selected from the group consisting of epoxy, halogen, methacrylate, vinyl, amine, allyl, phosphonate, styrlamine, and sulfide.

A predetermined amount of silanol condensation catalyst is added along with a predetermined amount of polymer, the polymer being selected from the group consisting essentially of a water soluble polymer, a water soluble copolymer, an alcohol soluble polymer, an alcohol soluble copolymer, and combinations of such polymers.

Thereafter the combination is stirred for a period of time of 15 hours or less at a temperature of 100° C. or less, wherein the incipient silane is present in the amount of 0.1 to 25 weight percent based on the amount of siliceous substrate and wherein the silane is present in an excess with regard to the total amount of reactive silanol groups of the siliceous substrate.

There is yet another embodiment that is a process for preparing a crosslinked polymer that is chemically bonded to the surface of a siliceous substrate, the process comprising heating a predetermined amount of alcohol in a reaction vessel with stirring, wherein the alcohol has from 1 to 9 carbon atoms.

Thereafter, adding a predetermined amount of a hydrolysis catalyst selected from organic acids having from 1 to 7 carbon atoms and adding a predetermined amount of a silanol condensation catalyst.

Then, there is added a predetermined amount of siliceous substrate containing reactive silanols and a predetermined amount of silane coupling agent, said silane being an alkoxy-functional silane having the general formula $$(RO)_3SiQX$$

wherein R is a hydrocarbon group having from 1 to 6 carbon atoms, Q is a hydrocarbon group having from 0 to 6 carbon atoms, and X is a functional group selected from the group consisting of epoxy, halogen, methacrylate, vinyl, amine, allyl, phosphonate, styrlamine, and sulfide.

Thereafter, adding a predetermined amount of polymer, the polymer being selected from the group consisting essentially of a water soluble polymer, a water soluble copolymer, an alcohol soluble polymer, an alcohol soluble copolymer, and combinations of such polymers.

The combination is then stirred for a period of time of 12 hours or less at a temperature of 75° C. or less, wherein the ratio of polymer to siliceous substrate is in the range of P:S wherein P is 0.1 to 50 and S is 99.9 to 50, wherein the incipient silane is present in the amount of 0.1 to 25 weight percent based on the weight of siliceous substrate and wherein the incipient silane is present in an excess with regard to the total amount of reactive silanol groups on the siliceous substrate.

There is a further embodiment that is a process for preparing a cross linked polymer that is chemically bonded to the surface of a siliceous substrate, said process comprising heating a predetermined amount of alcohol and water in a reaction vessel with stirring, wherein the alcohol has from 1 to 9 carbon atoms and wherein the ratio of alcohol to water is in the range of 99 to 1:1 to 99.

There is then added a predetermined amount of a hydrolysis catalyst selected from organic acids having from 1 to 7 carbon atoms and then there is added a predetermined amount of a silanol condensation catalyst.

A predetermined amount of siliceous substrate having silanols on the surface is then added along with a predetermined amount of silane coupling agent, said silane being an alkoxy-functional silane having the general formula $$(RO)_3SiQX$$

wherein R is a hydrocarbon group having from 1 to 6 carbon atoms, Q is a hydrocarbon group having from 0 to 6 carbon atoms, and X is a residue from a functional group selected from the group consisting of epoxy, halogen, methacrylate, vinyl, amine, allyl, phosphonate, styrlamine, and sulfide.

Thereafter there is added a predetermined amount of polymer, said polymer being selected from the group consisting essentially of a water soluble polymer, a water soluble copolymer, an alcohol soluble polymer, an alcohol soluble copolymer, and combinations of such polymers.

The combination is then stirred for a period of time of 15 hours or less at a temperature of 75° C. or less, wherein the ratio of polymer to siliceous substrate is in the range of P:S wherein P is 0.1 to 50 and S is 99.9 to 50, wherein the incipient silane coupling agent is present in the amount of 0.1 to 25 weight percent based on the weight of siliceous substrate and wherein the incipient coupling agent silane is present in an excess with regard to the total amount of reactive silanol groups on the siliceous substrate.

In another embodiment, there is a process for preparing a crosslinked polymer that is chemically bonded to the surface of a siliceous substrate. The process comprises heating a predetermined amount of water in a reaction vessel with stirring.

Thereafter there is added a predetermined amount of a siliceous substrate having reactive silanols and then adding a predetermined amount of silane coupling agent to provide a silane linking material. The silane coupling agent is an alkoxy-functional silane having the general formula $$(RO)_3SiQX$$

wherein R is a hydrocarbon group having from 1 to 6 carbon atoms, Q is a hydrocarbon group having from 0 to 6 carbon atoms, and X is a functional group selected from the group consisting of epoxy, halogen, methacrylate, vinyl, amine, allyl, phosphonate, styrlamine, and sulfide.

A predetermined amount of silanol condensation catalyst is added along with a predetermined amount of polymer, the polymer being selected from the group consisting essentially of a water soluble polymer, a water soluble copolymer, an alcohol soluble polymer, an alcohol soluble copolymer, and combinations of such polymers.

Thereafter the combination is stirred for a period of time of 15 hours or less at a temperature of 100° C. or less, wherein the incipient silane coupling agent is present in the amount of 0.1 to 25 weight percent based on the amount of siliceous substrate and wherein the silane coupling agent is present in an excess with regard to the total amount of reactive silanol groups of the siliceous substrate.

There is yet another embodiment that is a process for preparing a crosslinked polymer that is chemically bonded to the surface of a siliceous substrate, the process comprising heating a predetermined amount of alcohol in a reaction vessel with stirring, wherein the alcohol has from 1 to 9 carbon atoms.

Then, there is added a predetermined amount of siliceous substrate containing reactive silanols and a predetermined amount of silane coupling agent, said silane coupling agent being an alkoxy-functional silane having the general formula

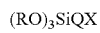
(RO)$_3$SiQX wherein R is a hydrocarbon group having from 1 to 6 carbon atoms, Q is a hydrocarbon group having from 0 to 6 carbon atoms, and X is a functional group selected from the group consisting of epoxy, halogen, methacrylate, vinyl, amine, allyl, phosphonate, styrlamine, and sulfide.

Thereafter, adding a predetermined amount of polymer, the polymer being selected from the group consisting essentially of a water soluble polymer, a water soluble copolymer, an alcohol soluble polymer, an alcohol soluble copolymer, and combinations of such polymers.

The combination is then stirred for a period of time of 12 hours or less at a temperature of 75° C. or less, wherein the ratio of polymer to siliceous substrate is in the range of P:S wherein P is 0.1 to 50 and S is 99.9 to 50, wherein the incipient silane coupling agent is present in the amount of 0.1 to 25 weight percent based on the weight of siliceous substrate and wherein the incipient silane coupling agent is present in an excess with regard to the total amount of reactive silanol groups on the siliceous substrate.

There is a further embodiment that is a process for preparing a cross linked polymer that is chemically bonded to the surface of a siliceous substrate, said process comprising heating a predetermined amount of alcohol and water in a reaction vessel with stirring, wherein the alcohol has from 1 to 9 carbon atoms and wherein the ratio of alcohol to water is in the range of 99 to 1:1 to 99.

There is then added a predetermined amount of a hydrolysis catalyst selected from organic acids having from 1 to 7 carbon atoms and then there is added a predetermined amount of a silanol condensation catalyst.

A predetermined amount of precipitated siliceous substrate having silanols on the surface is then added along with a predetermined amount of silane coupling agent, said silane being an alkoxy-functional silane having the general formula

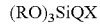
(RO)$_3$SiQX wherein R is a hydrocarbon group having from 1 to 6 carbon atoms, Q is a hydrocarbon group having from 0 to 6 carbon atoms, and X is a residue from a functional group selected from the group consisting of epoxy, halogen, methacrylate, vinyl, amine, allyl, phosphonate, styrlamine, and sulfide.

Thereafter there is added a predetermined amount of polymer, said polymer being selected from the group consisting essentially of a water soluble polymer, a water soluble copolymer, an alcohol soluble polymer, an alcohol soluble copolymer, and combinations of such polymers.

The combination is then stirred for a period of time of 15 hours or less at a temperature of 75° C. or less, wherein the ratio of polymer to siliceous substrate is in the range of P:S wherein P is 0.1 to 50 and S is 99.9 to 50, wherein the incipient silane coupling agent is present in the amount of 0.1 to 25 weight percent based on the weight of siliceous substrate and wherein the incipient silane coupling agent is present in an excess with regard to the total amount of reactive silanol groups on the siliceous substrate.

Other embodiments include a method of process stream purification, the method comprising treating a process stream effluent using a composition disclosed herein including removing metal ions and acids; a method of cleaning a waste stream, the method comprising treating a waste stream using a composition as disclosed herein, including removal of acids and metal ions; a method of recovering resources, the method comprising treating a fluid containing said recoverable resources with a composition as disclosed herein including recoverable resources such as metals and acids.

A further embodiment of this invention is a method for the recovery of metals selected from the group consisting of transition metals selected from i. silver, ii. gold, iii. cadmium, iv. chromium, v. copper vi. hafnium, vii. iridium, viii. manganese, ix. molybdenum, x. niobium, xi. osmium, xii. palladium, xiii. platinum, xiv. rhenium, xv. rhodium, xvi. ruthenium, xvii tantalum, xviii. technetium, xix. titanium, xx. tungsten, xxi. zinc, xxii. iron, xxiii. zirconium and, heavy metals selected from the group consisting of a. barium, b. bismuth, c. cerium, d. lead, e. antimony, f. tin, g. thallium, h. uranium, j. radium, and k. plutonium.

Also considered an embodiment of this invention is a method of removing organic acids from a fluid, the method comprising treating the fluid with a composition as disclosed herein, said acids including, but not limited to, humic acid, pulvic acids, p-aminobenzoic acid, carboxylic acids, especially salicylic acid and acetasalicylic acid.

Further embodiments of this invention are anionic and cationic exchange resins prepared utilizing a composition as disclosed herein; a method of separating proteins and an analytical method of separating proteins wherein associated materials are also proteins.

Still further embodiments include an analytical method of separating peptides, the method comprising utilizing a composition of this invention, especially wherein the method is utilized to selectively adsorb or separate certain peptides from other associated peptides.

Yet other embodiments of this invention include a method of separating oligionucleotides from associated materials, the method comprising utilizing a composition as disclosed herein to adsorb said oligionucleotides, especially separating oligionucleotides from associated oligionucleotides.

Going to other embodiments of this invention, there is a method of concentrating anionic materials, the method comprising contacting the anionic materials with a composition as disclosed herein wherein the anionic materials to be concentrated are selected from the group consisting of i. molybdates, ii. arsenates, iii. phosphates, iv. dichromates, v. tungstates, vi. zirconates, vii. titanates, viii. cerates, ix. vanadates, x. arsenic, xi. complex anionic materials, and, xii. any combination of i. to xi.

There is still another embodiment that is removing dyes from waste water in dye processing plants. In an extensive embodiment, there is the scavenging or dye transfer inhibition of dyes on clothes in the home and institutional detergent washing of fabrics; removal of dyes from waste water from process waters of dye processing plants.

There is an embodiment of this invention that is a method of analysis, the method comprising utilizing a composition as disclosed herein for separating the desired material of analysis from materials associated with the desired material of analysis, for example, liquid chromatography, the method comprising utilizing a composition as disclosed herein as a filler in a column employed in the liquid chromatography process.

It has also been discovered by the patentees herein that the compositions disclosed herein are useful in personal care products such as deodorants, antiperspirants and cosmetic face creams where ion capture and fragrance controlled release are needed and, toothpastes wherein the toothpaste is based on gels or silica filled materials, especially nanosilicas.

Another embodiment of this invention is the capability of removing soluble crude oils including aliphatics, aromatics, and naphthenates from fluids.

DETAILED DESCRIPTION OF THE INVENTION

Turning now to the details of the instant invention and with specificity, there is disclosed herein a composition of matter that is a solid siliceous substrate that has bound to it, a polymer, using a silane coupling agent, with the further proviso that the bound polymer is crosslinked to provide cavities for the adsorption as well as the complexing or sequestering of various materials such as metals, proteins, acids, and the like.

The polymers useful in this invention include those polymers selected from the group consisting of water soluble polymers, water soluble copolymers, alcohol soluble polymers, alcohol soluble copolymers, and combinations of such polymers.

Especially useful in this invention are polyamine polymers, polyethyleneimines, acrylic polymers, polyols, including polymers containing only polyoxyethylene units, only polyoxypropylene units, and only polyoxybutylene units and, copolymers of such units. Also included are copolymers of acrylates and copolymers of styrene with other polymers.

Preferred for this invention are polyamine, polyethyleneimines and acrylic polymers and more preferred are the polyethyleneimines and the acrylic polymers. Most preferred for this invention are the polyethyleneimines. The polymers are used such that the incipient amount of the polymer used is from about 0.1 to 50 weight percent based on the weight of the siliceous substrate. The preferred amount of incipient polymer is in the range of from 1 weight % to about 30 weight % with the most preferred amounts being in the range of from about 5% to about 15%. The desired molecular weight for the polymers is in the range of 1000 to 200,000 Daltons. Calculations of polymer packing against silica size shows that one can sustain more polymer on smaller silica and by contrast, less polymer on larger silica. For example, it is within the scope of this invention to use 0.1% on 200 micron silica and 50% polymer on 0.1 micron, or 20 nanometer silica.

It should be understood by those skilled in the art that such polymers should have the capability of being further crosslinked after binding them to the siliceous substrates as is described herein in detail with regard to the polyethyleneimines.

It is well within the capability of the processes herein that the size of the cavities can be varied and controlled thereby providing a unique sequestering medium.

The solid particulate substrates useful in this invention are siliceous substrates that provide a stable —SiO— bond when bound to a silane coupling agent of this invention. Included in this group are any solid particulate materials that contain Si—O bonds and can be for example, silicas, including fumed, precipitated, and ground silicas, along with other forms such as silica gels and the like. The term "siliceous substrates" for purposes of this invention can also be mixtures of siliceous materials with other inorganic oxides, naturally occurring or synthetic silicates, alumina, naturally occurring materials that form stable bonds with silane coupling agents, as long as there are silanols available for the seminal coupling of the silane coupling agents to such substrates. Glass, especially porous glass, can also be used as the substrate, provided the glass is ground fine enough to fit the sizes of the particulate materials being used herein. Preferred for this invention are particulate materials having surface areas of from 3 to 330 $m^2$/gm when analyzed by light scattering analysis (colloidal analysis) wherein surface area is calculated on particle size.

Such siliceous substrates are commercial materials and can be obtained for example from Environ Degussa Corporation, located in Parsippany, N.J. and sold as SIPERNAT 22, SIPERNAT 35, SIPERNAT 350, and SIPERNAT 2200, among other silicas, Tixosil 68 available from Rhodia North America, Cranbury, N.J. and Cabot Cab-O-Sil M5 from the Cabot Corporation, Boston, Mass.

In addition, Envonik Degussa Corporation provides Sident 8 having a low surface area and average diameter of 10 micrometers, Sident 9 having a low surface area/absorption having an average diameter of 10.5 micrometer and Sident 10 having the lowest surface area and an average diameter of 10.5 micrometer, Ultrasil 360 having a low surface area and an average diameter of 28 nanometers, Sipernat 22HR having a high surface area with an average diameter of 100 micrometer, Sipernat 820A, a low surface area aluminum silicate with an average diameter of 4 micrometer, and Sipernat 880 a low surface area calcium silicate, having an average diameter of 8 micrometers. Rhodia North America Inc. provides Siloa 72X high surface area and an average diameter of 12 micrometers, Tixosil 365, having a medium surface area and an average diameter of 3 to 4 micrometers, Tixosil 43 having a high surface area and an average diameter of 10 micrometer, Tixosil 38 D, having a medium surface area and an average diameter of 100 micrometers, Tixosil 68 MP, having a high surface area and an average diameter of 250 micrometers. Cabot Corporation also provides Cab-O-Sil M-7D, a dense form of M-5 having a high surface area and an average diameter of 0.2 to 0.3 micrometer, Cab-O-Sil TS-610 a hydrophobic M-5 having a medium surface area and an average diameter of 0.2 to 0.3 micrometers.

W. R. Grace and Co., Baltimore, Md. provides Sylodent 650 XWA having a low surface area, non-porous, having an average diameter of 7 to 10 micrometers, Sylodent XWA 300 having a low surface area, non-porous, having an average diameter of 2 to 4 micrometers.

Nyacol Nano Technologies, Inc., Ashland, Mass. Provides Nyacol DP5480, a nano silica at about 50 nanometers-TEM, Nyacol DP5540 a nano silica at 100 nanometers-TEM, Nyacol DP5820, a nano silica at about 20 nanometers. Also, hanse chemie, Geesthacht, Nr Hamburg, Germany provides Nanocryl D, a nano silica having an average diameter of 20 nanometers-SANS.

Both acidic and basic siliceous materials can be used as the solid substrate herein, it being understood that the coupling of the silane coupling agent to the siliceous substrate is quite slow in a neutral or basic media, and therefore, it is judicious to use a hydrolysis catalyst to hasten the coupling reaction. Typically, with acidic siliceous substrates, hydrolysis catalysts do not need to be used, depending on the pH of the reaction media. For example, preferred for this invention are pH levels below 7, more preferred are pH levels below 5.4 and most preferred are pH levels below 4. Of course, hydrolysis catalysts can also be used with acidic siliceous substrates to enhance the reaction rate.

The polymers are bound to the siliceous substrates by the use of silane coupling agents. Silane coupling agents combine the organic chemistry of organofunctional groups with inorganic chemistry of silicates to bridge the hydrophilic interface between mineral substrates and organic molecules and polymers.

The most useful silane coupling agents for this invention are the silane coupling agents having the general formula (RO)SiQX wherein R is a hydrocarbon group having from 1 to 6 carbon atoms, Q in each case is a hydrocarbon group having from 0 to 6 carbon atoms, X is a functional group selected from the group consisting of epoxy, halogen, methacrylate, vinyl, amine, allyl, phosphonate, styrlamine, and sulfide, wherein the residual silane material as a result of the hydrolysis is $O_{3/2}SiQY$, wherein Q in each case is a hydrocarbon group having from 0 to 6 carbon atoms, and Y is a functional group selected from the group consisting of epoxy, halogen, methacrylate, vinyl, amine, allyl, phosphonate, styrlamine, and sulfide.

One of the most preferred is the silane coupling agent having the general formula

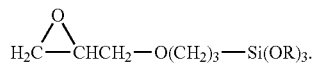

Most preferred of this general formula is the silane coupling agent:

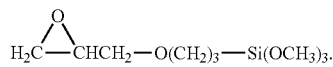

For purposes of this invention, the incipient amount of the silane coupling agent to be used is about 0.1 to 25 weight percent based on the weight of the siliceous substrate. Preferred are incipient amounts ranging from about 2 weight percent to about 10 weight percent, however, this is dictated by the fact that the silane coupling agent used is based on the amount of silanols on the siliceous substrate, in that, the silane coupling agent is used in an excess over that required to bind the polymer to the siliceous substrate. The excess of the silane coupling agent is then used in the process to cross link the polymer that is actually bound to the solid surface, that is, any excess silane coupling agent is reacted with some of the reactive groups on the polymer that are not utilized to chemically bond the polymer with the siliceous substrate.

Upon hydrolysis, in the presence of the solid substrate, the silane coupling agent hydrolyzes, that is the $(CH_3O)$— groups are cleaved from the silicon and are replaced by silanols, that is —SiOH groups. Initially, the material that is formed is the trisilanol, i.e. $XQSi(OH)_3$, which then condenses with the silanol groups on the solid substrate.

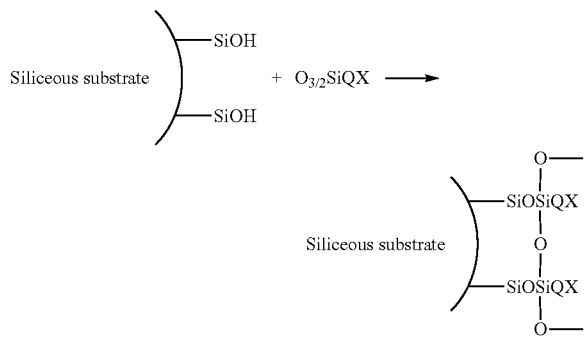

Figure 7:
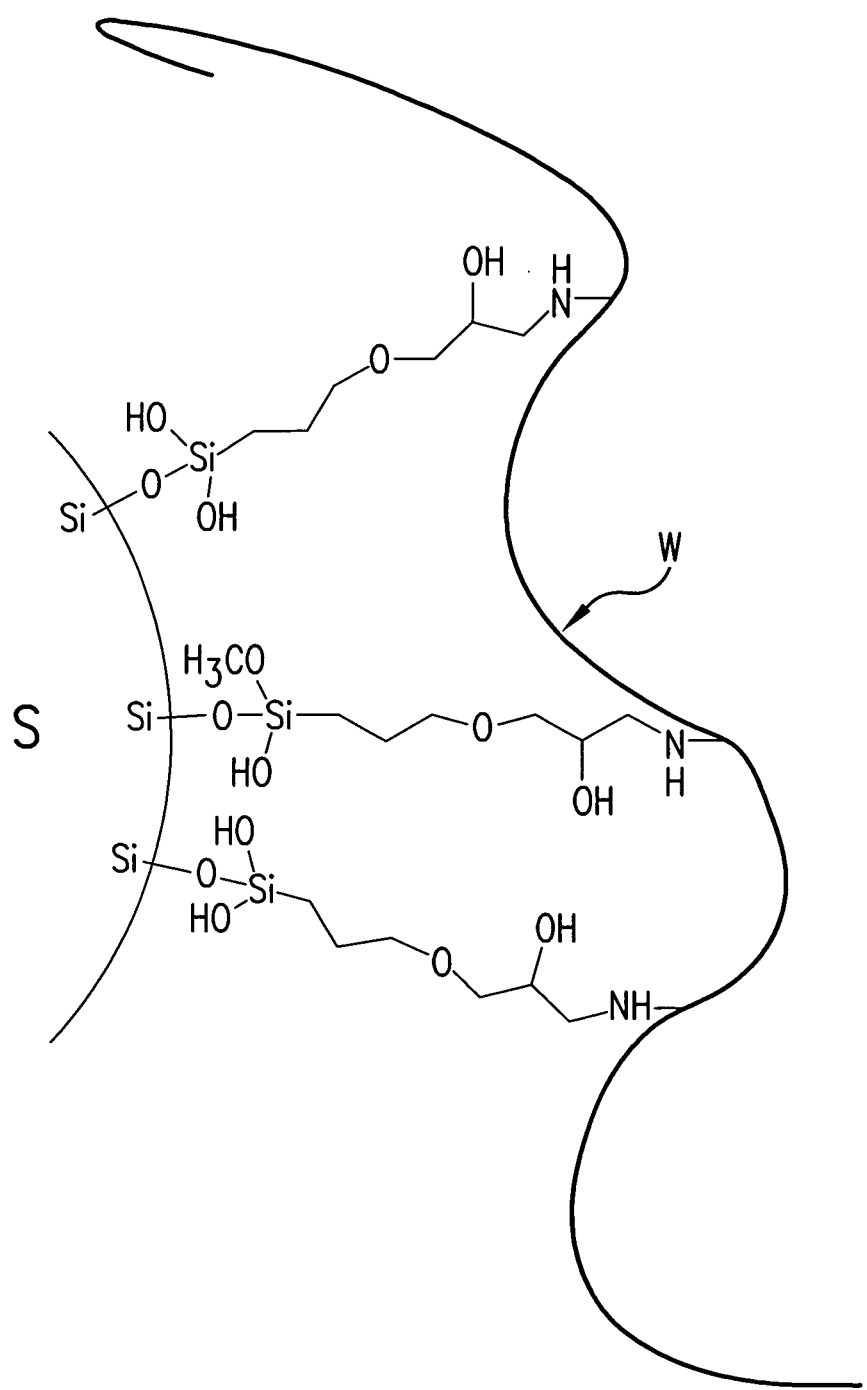
FIG. 7 is an illustration of the silica particle with the silane attached and the PEI polymer attached to the silane linker as an example of the Rosenberg molecule wherein the hyperbole S is the silica and the long wavy line W is the linear Rosenberg polymer.
Figure 8:
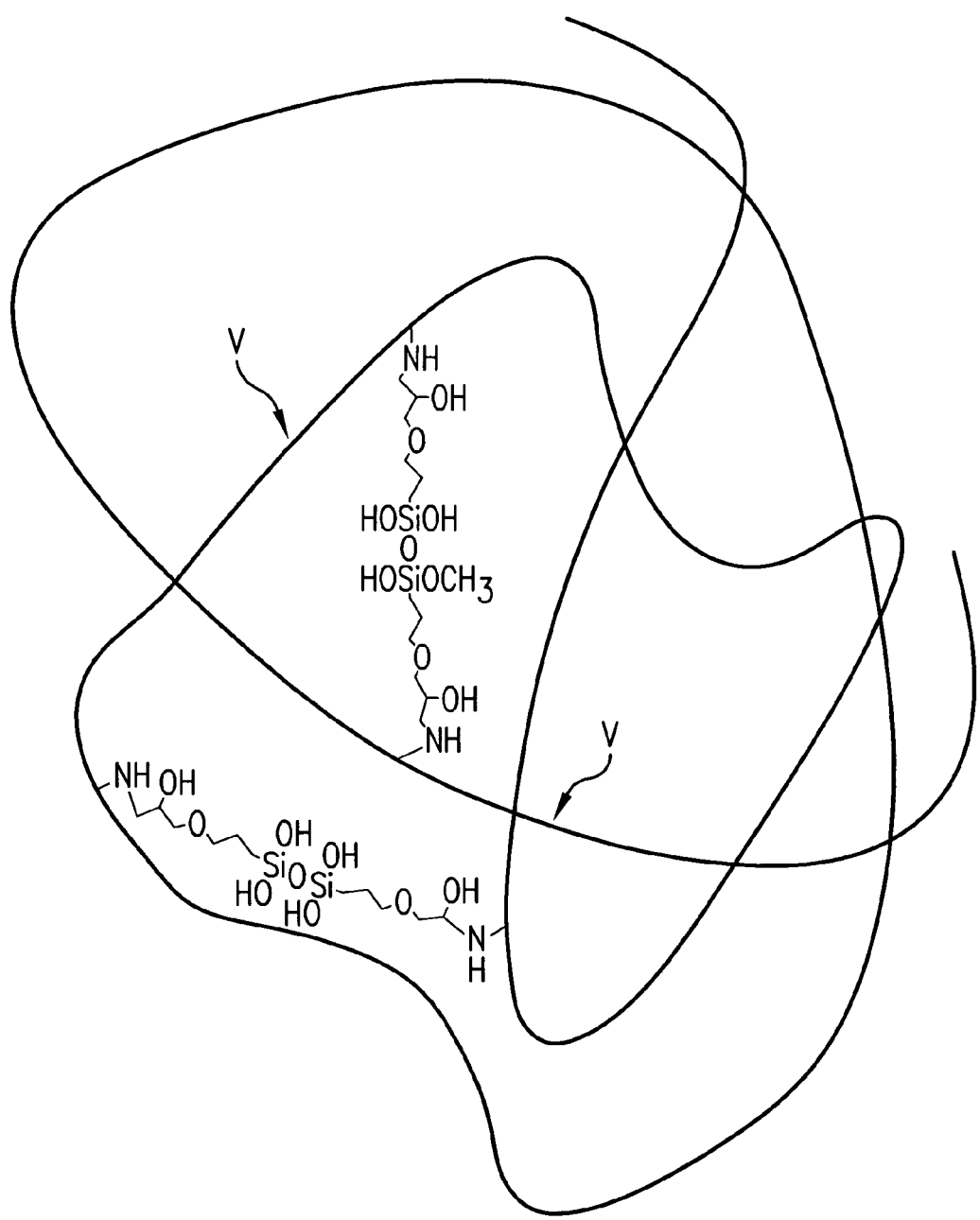
FIG. 8 is an illustration of the PEI polymer attached to the silane linker and crosslinked. The attachment to a siliceous substrate is not shown (see FIG. 6). The intertwined wavy lines V are the polymer strands.

See also FIG. 7.

Figure 6:
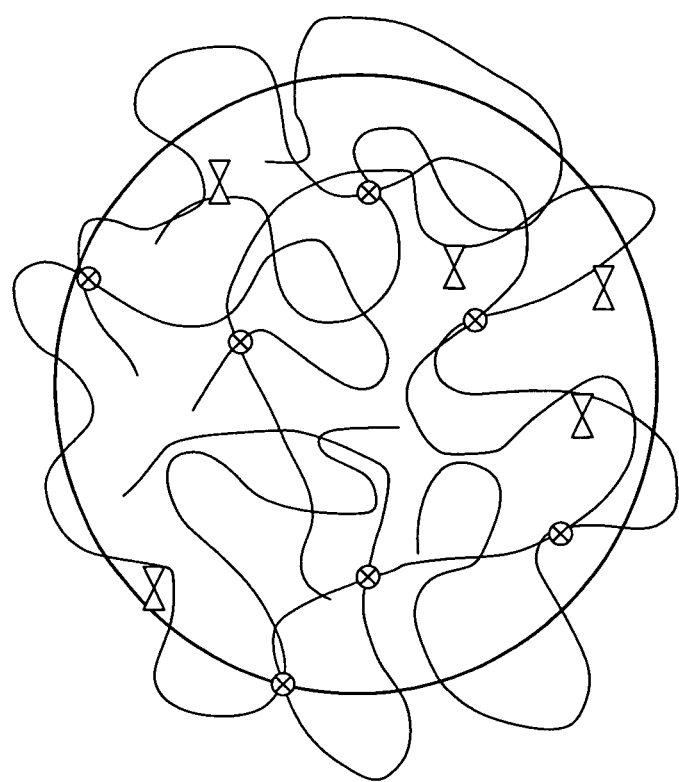
FIG. 6 is a depiction of a silica particle treated according to the process of this invention wherein O is the silica particle,  is the attachment points of the polymer to the silica surface by linker molecules, ⊗ the cross link points along the polymer chains, and 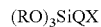 is the PEI polymer chains.

The polymers are then bound to the silane coupling agent through the reaction of X with functional groups on the polymer. FIG. 6 is a depiction of a silica particle treated according to the process of this invention wherein O is the silica particle, ✖ is the attachment points of the polymer to the silica surface by linker molecules, ⊗ is the cross link points along the polymer chains, and ✿ is the PEI polymer chains.

For purposes of this invention, it should be noted that there are several related processes by which the compositions of this invention can be prepared.

The first process is a process for preparing a crosslinked polymer that is chemically bonded to the surface of a siliceous substrate. The process uses water as the reaction media. A predetermined amount of water is heated in a reaction vessel with stirring and a predetermined amount of a hydrolysis catalyst, that is, an organic acid, is added. The catalyst has 1 to 7 carbon atoms. The most preferred acid is acetic acid.

Thereafter, a predetermined amount of a siliceous substrate having reactive silanols is added to the reactor along with a desired silane coupling agent. The silane is added in amounts that will provide for the binding of the silane to the substrate, provide for binding of the desired amount of polymer to the silane linking material, and an excess of the silane to crosslink the polymer.

After a short period of time, there is added a silanol condensation catalyst and a predetermined amount of the desired polymer. Preferred condensation catalysts for this invention include alkylbenzylsulfonic acids, such as toluene sulfonic acid; alkyl titanates, such as tetraisopropyltitanate, tetraethyltitanate, tetrabutyltitanate, and n-propyltitanate.

Thereafter, the combination is stirred for a period of time of 15 hours or less, and it should be noted by those skilled in the art that this time period is much less than that of the prior art processes. Also, the process is run at a temperature of 100° C. or less, even as low as 50° C., and this should also be noted by those skilled in the art as being significantly less than the processes of the prior art.

Thereafter, the product can be packaged as a slurry, or it can be spray dried to a powder. In this case the powders are free flowing and white in color.

A second process is one in which the water of the process is substituted by an alcohol as the reaction medium, wherein the alcohol is a non-aromatic alcohol solvent having from 1 to 9 carbon atoms. Thus, alcohols useful in this invention include ethanol, propanol, isopropanol, and the like, and mixtures of these alcohols.

In addition, the reaction conditions vary from those set forth Supra in the water process, in that, the period of time for stirring and reaction is 12 hours or less and the temperature of the reaction is at 75° C. or less. A further limitation is the ratio of the polymer to the siliceous substrate. The ratio of polymer (P) to siliceous substrate (S) is such the P is 0.1 to 50 and S is 99.9 to 50.

In a third process, the alcohol and water are both used for the reaction medium for the reaction. In this process, it should be noted that the alcohol to water ratio should be in the range of 99:1 to 1:99. The reaction conditions also differ from the other two processes set forth Supra, in that, the period of time for the reaction is 15 hours or less and the temperature is on the order of 75° C. or less. The ratio of the P:S is the same as in the alcohol process.

Each of these three processes can be carried out without the aid of a hydrolysis catalyst.

Preparation of the Filtration Column for Lab Filtration Studies

A glass column was provided that would accommodate the volumes of water that needed to be used to conduct the tests. This was predetermined by the tester. In this case, the columns were cleaned glass and were either 2 cm diameter and 24 to 25 cm long or 4 cm diameter and 25 cm long. The 2 cm has a 1 liter filtrate volume with a water head of 10 to 20 cms while the latter has a volume of 1 to 2 liters and a water head of about 10 cms.

The column is first cleaned in hot water and excess water is shaken from the column after allowing hot water to flow through the column tip to remove any old water soluble materials. A small piece of glass wool is inserted in the bottom of the column and packed evenly at the bottom or over the frit if the column contains frit, but not unreasonably compressed. The best column is one that is actually frit free because the flit can become blocked and slow the filtrate flow rate when any particle or sub-particles block the frit pores.

The glass wool is tapped into a thin layer about 2 mm thick evenly across the column base. Hot water is then run through the glass wool to remove any water-soluble stray elements. Then, 0.5 liters of deionized water is used to flush the column and this discharge is discarded. Samples are taken as a reference just before the volume reaches 10 mls above the glass wool. The glass wool was not allowed to dry thereafter. The slurry was diluted with deionized water until it flowed with even consistency.

In the 2 cm diameter vs. 25 cm long column, 75 mls of the slurried product was poured, which slurry holds about 25 gms of silica and about 59 gms of water. The excess water is allowed to drain though the glass wool and collect for weighing and is then discarded. The filter bed was washed with at least 1 liter of deionized water and the filtrate was now crystal clear and samples are taken at this point. The drop rate was checked against a clock and the time noted.

The slurry volume was poured in one action of delivery to avoid layering and the product was allowed to settle as the excess water flowed through the packing bed. This technique avoided channels at the glass column walls. The column was not allowed to dry out so there was always a header of water above the column per se.

Deionized water was continually passed through the column such that at least 2 liters in total passed and it was collected and discharged (taking another sample just prior to the last 100 mls elution). The pre-prepared copper solution was added to the header vessel in a way that did not disturb the column bed per se and the water phase was allowed to run onto the bed.

The top layer showed blue almost immediately indicating that the Cu has reached the packed bed. The clock was started and when the receiver was full, it was taken as a sample. This left the receiving vessel with zero volume.

The filtrate was allowed to collect and the volume filtrate volume noted against the time, remembering that the typical Void Volume for this 2 cm diameter vs 24 cm long bed was about 50 mls. Every 50 mls means that one has captured the metal cations on the bed rather than having them flowing through the bed.

The top of the upper reservoir vessel was continually filled to maintain water pressure head as the blue color and copper transgressed down the column. When the blue reached the bottom glass wool, the metal breakthrough was reached and the time recorded. Samples were taken at every 200 mls flow rate which would be typically 4 to 5 Void Volumes. The flow rate was recorded in terms of drops per time throughout to ensure the flow rate was consistent.

To the human eye, the copper sulphate solution appears colorless at the 10 to 100 ppm concentration. However, when the copper is absorbed from the solution into the polymer layer grafted to the silica particles, then it concentrates the copper and the polymer coating turns blue. This color intensity increases with the polymer loading of copper. This confirms the binding of metals such as copper. By concentrating the copper, and turning the polymer layer blue, then the whole particle appears deep blue. This allows one the visual means to follow the binding of the copper in a qualitative manner and it shows where the copper is bound and where the copper is not bound. In other words, this allows one a visual way to follow the front of cleaning trace contaminated solutions as they pass through the packed bed column.

The top layer showed blue almost immediately indicating that the Cu has reached the packed bed. The clock was started and the filtrate was allowed to collect and the volume filtrate volume noted against the time, remembering that the typical Void Volume for this 2 cm diameter vs. 24 cm long bed was about 50 mls. Every 50 mls means that one has captured the metal cations on the bed rather than having them flowing through the bed.

The top of the upper reservoir vessel was continually filled to maintain water pressure head as the blue color and copper transgressed down the column. When the blue reached the bottom glass wool, the metal breakthrough was reached and the time recorded. Samples were taken at every 200 ms flow rate which would be typically 4 to 5 Void Volumes. The flow rate was recorded in terms of drops per time throughout to ensure the low rate was consistent.

Figure 9:
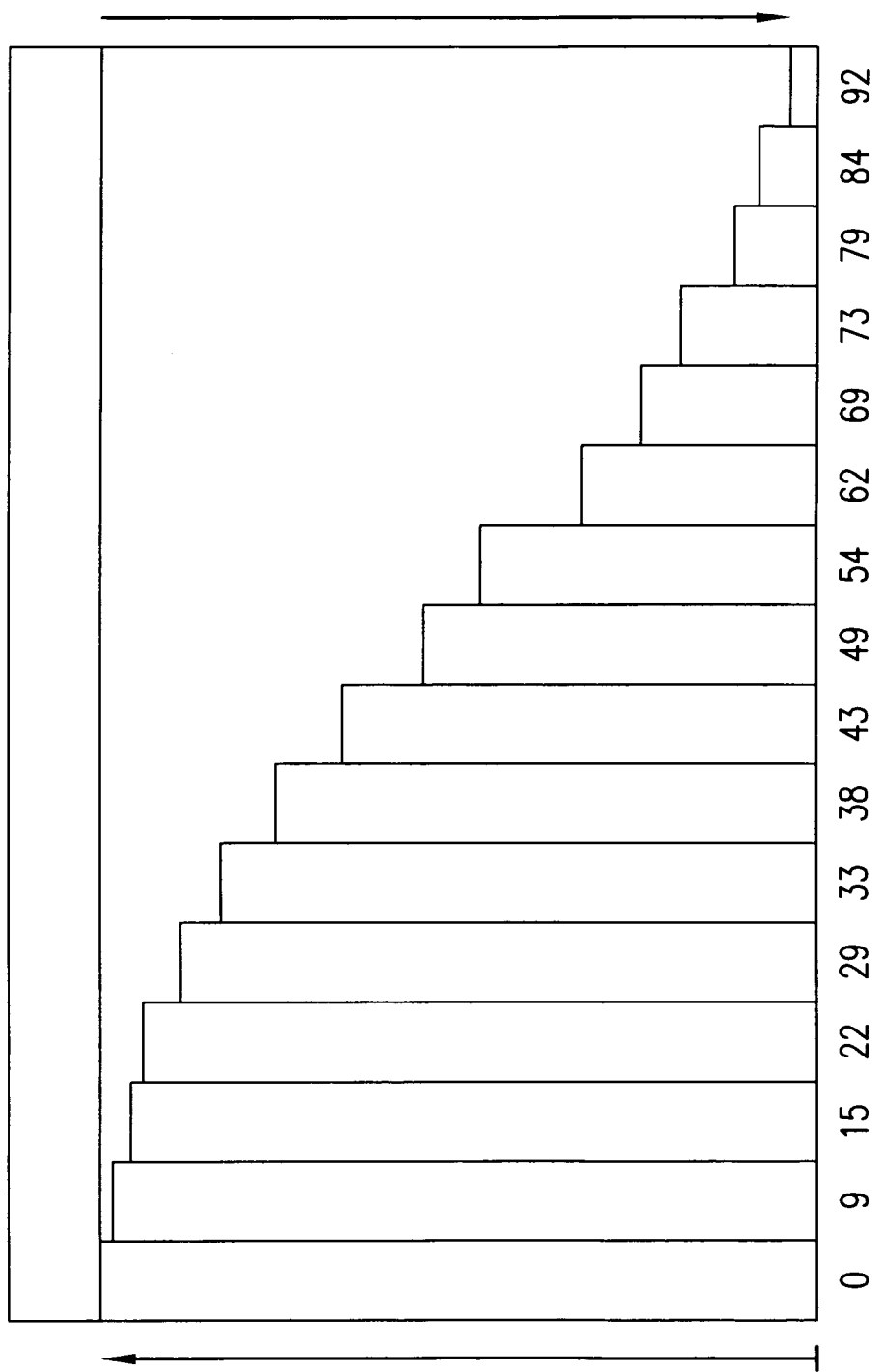
FIG. 9 is a representation of a packed bed column treating copper sulphate solution wherein there is used a 10 weight % polymer bound to 100 micron silica.

FIG. 9 is a histogram representation of data obtained from a packed bed column of a material of this invention which is a solid silica that has bound to its surface, 10 weight % of PEI and the silica is SIPERNAT 22, 100 microns in size, packed into the glass column as a slurry as outlined in the methodology of preparing the column for filtration studies set forth Supra. The left hand ordinate is column height with 10 ppm of copper solution flux and the right hand ordinate is the increased packed bed column saturation with copper. The abscissa is the flux in terms of void volumes.

In this representation, the column consisted of a flowing stream of 10 ppm copper as copper sulfate in tap water, creating a 25 cm head pressure on the column. The elements represent the state of the column after an increasing number of void volumes of fluid have passed through the bed. The void volume is that liquid volume in the bed not occupied by silica or polymer. Typically this void volume is some 60 to 70% of the packed column volume dependent upon the silica distribution and particle size.

As the copper solution flows by gravity through the packed bed, the copper binds to the polymer macro-voids created in the grafting of the polymer onto the surface of the chosen silica as it is being removed from the water phase. The phase continued to pass through the column bed and was collected at the bottom of the bed and contained less than parts per billion (ppb) Cu and even as low as single digits parts per trillion (ppt) of Cu.

The column continues to bind copper as long as the bound copper "front" is above the bottom of the column. When the "copper front" reaches the bottom of the bed, the copper bed "breaks through" and as such that bed was now fully spent and was replaced by removal or in-situ re-generation by back flowing with acidic wash water of pH of about 2.

Figure 10:
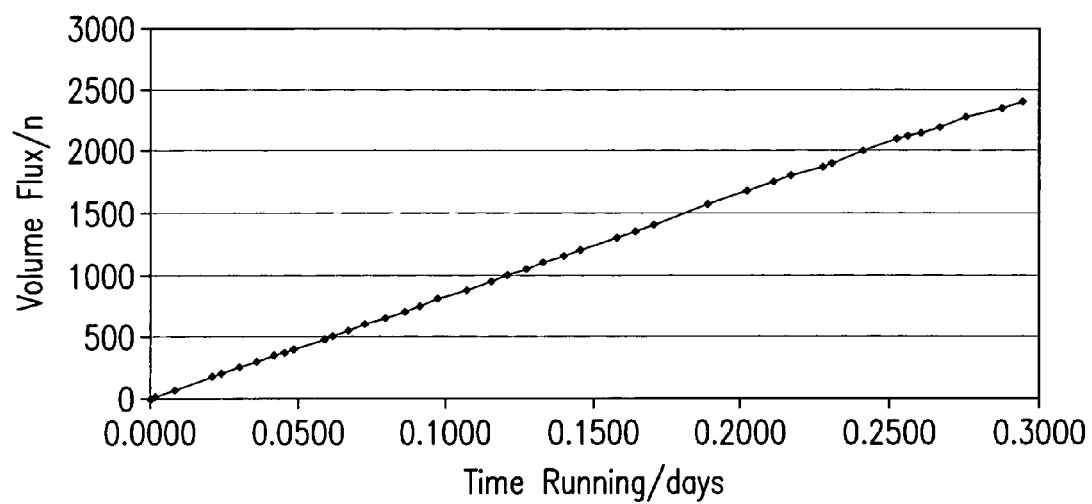
FIG. 10 shows the elution of 100 ppm of Cu as $CuSO_4$ through a composition of this invention which is a silica substrate having 20 weight % polymer bound to 250 micron silica wherein the ordinate axis in "Volume flux in mls" and the Abscissa is time in days/running time.

The total amount of copper actually bound in the packed bed column ranged from 20% to 5% by weight of polymer grafted to the silica surface. The flux rate throughout a typical experiment is shown in FIG. 10. The ordinate is Volume Flux in milliliters and the abscissa is Time Running in days. The glass column was established as 2 cm diameter and 24 cm tall above the glass wool packed from a slurry. Column feed was 100 ppm Cu as copper sulfate in deionized water via header set at 5 cm water head. (Flux/mls with time/days). There is shown therein the linear flux rates for 100 ppm cu as copper solution flowing through a packed glass column with a material that is solid silica supplied by Rhodia as Tixosil 68 containing 20 weight percent of PEI on 250 micron silica. The flux was essentially linear based on time and also based on void volumes exchanged throughout this period. The flux continued linear even after the copper effected breakthrough as the copper front left the packed bed column.

The polymers used in the examples were polyethyleneimines having the general formula $\{-H_2C-CH_2-NH-\}_x$ obtained from BASF Corporation, Mount Olive, N.J., USA and consist of Lupasol WF, Lupasol HF and Lupasol G500. Lupasol WF is water free and has a molecular weight of 25,000 having a pH of 11. Lupasol HF is in water at 56 weight % having a viscosity of 11,000, a molecular weight of 25,000 and a pH of 11. Lupasol G500 is in water at 40 weight % having viscosity of 1,000 and a molecular weight of 25,000.

One silane used herein was Dynasylan® GLYMO which is 3-glycidoxypropyltrimethoxysilane having a molecular formula of

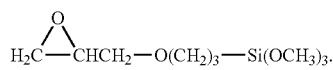

Also used herein was a similar silane known as Dow Corning® Z6040 which was obtained from the Dow Corning Corporation, Midland, Mich. USA having the same formula. The reaction of this invention can be carried out in glass reactors, glass lined reactors, steel reactors, but not mild steel reactors.

All spectrometer determinations in these examples were taken on an Agilent diode array UV spectrometer, model 8453, supplied by Agilent Corporation, Santa Clara, Calif.

EXAMPLE 1 Reaction in Ethanol and Water

Preparation of stock polymer solution (A) was carried out by adding 30 Kgms reagent grade ethanol to 0.90 Kg Lupasol WF with stirring to produce a homogeneous solution.

Nine Kgms of Sipernat 35 silica was charged to a reactor. Then, 50 Kgms of reagent grade ethanol were charged to the reactor slowly with stirring to aid dispersion. An additional charge of 50 Kgms of ethanol was charged to the slurry and the reaction mass was continually stirred while heating to 65° C. and the reactor was held at that temperature. There was then added 0.18 Kgms of deionized water and the stirring was continued for about 15 minutes. Toluene sulfonic acid, 45 gms, was added and the reaction mass allowed to stir for an additional 30 minutes while heating to 75° C. to drive off water from the reaction mass.

There was then slowly added 1.2 Kgms of 3-glycidoxypropyltrimethoxysilane to the reactor and the reaction mass was allowed to stir for an additional 30 minutes and held at 65° C.

The stock polymer solution (A) prepared as above was added to the stirred reactor over a period of thirty minutes. The reaction mass was allowed to stir and the reactor was held at 50° C. for a period of one additional hour (a total of 1.5 hours). The temperature was increased to remove the ethanol while replacing with equal volumes of deionized water. When the ethanol had been removed, the product was now about a 50% dispersion and was cooled.

This product was spray dried to obtain a fine white powder.

EXAMPLE 2

Seven and ½ Kgms of Lupasol G500 (a 40% by weight polymer solution supplied in water) was added to a glass vessel and stirred to ensure a homogeneous solution.

Four Kgms of deionized grade water was added to a glass vessel and then 3.0 Kgms Lupasol WF was added and the mixture was stirred to produce a homogeneous solution. This was stock polymer solution (A).

One hundred Kgms of water was charged to a reactor while heating to 75° C. There was then charged 30 Kgms of SIPERNAT 350 silica with minimal stirring, enough to just avoid settling. The temperature was maintained at 75° C. There was then charged 5 Kgms of deionized water and 300 gms of acetic acid and the mixture was continually stirred for about 10 minutes at 75° C.

There was then slowly added 3.6 Kgms of silane (Z6040) to the reactor and the mixture was stirred for 10 minutes with the reactor held at 75° C. Thereafter there was added 100 gms of toluene sulfonic acid and the mixture was stirred for an additional 30 minutes.

The stock polymer solution (A) was added to the stirred reactor over a period of 30 minutes while the reactor was held at 75° C. Thereafter, the reactor was stirred and held at 75° C. for a period of one additional hour or a total of 1.5 hours. The slurried product of about 40% solids dispersion was allowed to cool and then spray dried to a fine white powder.

EXAMPLE 3

This example was the preparation of 10 weight % PEI on 250 micron precipitated silica. Materials included 5.0 Kgms of Rhodia Tixosil 68, 12 liters of deionized water, 50 ml of glacial acetic acid, 500 ml of Dynasylon GLYMO, 50 gms of toluene sulfonic acid, and a polymer stock solution (500 gms of Lupasol WF (PEI polymer) dissolved in 2 liters of deionized water using the following procedure.

The 12 liters of water was preheated to near boiling. Thereafter, the silica was weighed and added to the 20 liter reactor. Then, preheated water was added with stirring and the acetic acid was added. After 15 minutes, the GLYMO was added and then after 30 minutes, the toluene sulfonic acid was added. After 45 minutes, the PEI was added and after 2.5 hours, the material was drained into a 5 gallon carboy as a white slurry.

EXAMPLE 4

This example was the preparation of 10% polyethyleneimine on 250 micron precipitated silica using 5.0 Kgms Rhodia Tixosil® 68, 16 liters of deionized water, 50 ml of glacial acetic acid, 500 ml of Degussa Dynasylon GLYMO, 50 gms of toluene sulfonic acid, 500 gms of BASF Lupasol WF, and PEI in one liter of deionized water.

Sixteen liters of the water was preheated to near boiling. Then the silica was weighed in and added to a 20 liter reactor. Then, preheated water was added with stirring along with the acetic acid. After 15 minutes, the GLYMO was added and then after 30 minutes, toluene sulfonic acid was added. After 45 minutes, the PEI was added, and after 2.5 hours of reaction time, the material was drained as a white slurry into two 2.5 gallon glass carboys.

EXAMPLE 5

This is the preparation of 10 weight % PEI on 250 micron precipitated silica.

The materials were 4.0 Kgms Degussa Sipernat 2200, 16 liters of deionized water, 40 ml of glacial acetic acid, 400 ml of Degussa Dynasylon GLYMO, 40 gms of toluene sulfonic acid, 400 gms of BASF Lupasol WF.

The water, all 14 liters, was preheated to near boiling in a reactor. Acetic acid was then added and the silica was weighed in. Thereafter, one liter of heated water was added with stirring. After 15 minutes, GLYMO was added and the stirring continued. After 30 minutes, toluene sulfonic acid was added with stirring, and after 45 minutes, PEI was added in one liter of water.

After 2.5 hours, the material was drained into 5 gallon carboys and consisted of a white slurry.

EXAMPLE 6

A second batch of 10 weight % of PEI on 250 micron precipitated silica was prepared using 4.0 Kgms of Degussa Sipernat 2200, 16 liters of deionized water, 40 ml of glacial acetic acid, 400 ml of Degussa Dynasylon GLYMO, 40 gms of toluene sulfonic acid, 400 gms of BASF Lupasol WF (PEI).

The procedure was as in Example 5 and a white slurry was obtained.

EXAMPLE 7

Another batch of 10% PEI on 250 micron precipitated silica was prepared. The materials were 4.0 Kgms of Rhodia Tixosil 68, 14 liters of deionized water, 40 ml of glacial acetic acid, 400 ml of Degussa Dynasylon GLYMO, 40 gms of toluene sulfonic acid and 1 liter of BASF Lupasol G500 (a 40 weight % PEI in supplied) water diluted with 1.5 liters of deionized water as a stock polymer solution.

The procedure was the following. Fourteen liters of preheated water (75° C.) was added to the reactor along with the acetic acid. Then silica was weighed into the reactor. After 15 minutes, GLYMO was added and after 30 minutes, toluene sulfonic acid was added. After 45 minutes, the stock solution of PEI solution was added. After 2.5 hours of stirring time, the material consisting of a white slurry was drained into a 5 gallon carboy.

EXAMPLE 8

Another batch of 10% PEI on 0.2 micron precipitated silica was prepared in a manner consistent with Example 7 in which the materials were 4.0 Kgms of Cabot M-5, 0.2 micron silica, 15 liters of deionized water, 80 ml of glacial acetic acid, 800 ml of Degussa Dynasylon GLYMO, 80 gms of toluene sulfonic acid, 1 liter of BASF Lupasol G500 (a 40 weight percent solution of PEI in supplied water) diluted to 3 linters with deionized water. The result was a white slurry.

EXAMPLE 9

Another batch of materials was made by charging the following ingredients into a 100 gallon reactor.

A stock polymer solution (A) was prepared by adding 40 Kgms of water to 0.03 Kgms of Lupasol WF and stirring to provide a homogeneous solution.

While heating the reactor to 75° C., it was charged with 100 Kgms of water. There was charged 30 Kgms of SIPERNAT 350 silica with minimal stirring to avoid settling and in order to maintain the temperature at 75° C.

Thereafter, there was charged 5 Kgms of deionized water and 3 gms of acetic acid and the reaction mass was continually stirred for about 10 minutes at the prevailing temperature. There was then slowly added 0.036 Kgms of silane (Dow Corning Z6040) to the reactor and it was stirred for 10 minutes with the reactor still held at 75° C. There was then added 100 gms of isopropyltitanate and the reaction was stirred for an additional 30 minutes.

Thereafter, the stock polymer solution was added over a period of 30 minutes while the temperature was held at 75° C. The reaction was stirred at that temperature for an additional one hour or a total of 1.5 hours. There was obtained a white slurry product that was cooled and packaged. Thereafter, the slurry was spray dried to obtain a white powder.

EXAMPLE 10

A comparison example and not within the scope of this invention

This example is essentially the preparation of a material from U.S. Pat. No. 6,803,106, that issued on Oct. 12, 2004, the first layer only, using toluene as a solvent. This example illustrates the many, many steps required by the '106 patent process, along with an illustration of the long time required to obtain a material which is a twin solvent, multistage layer deposition process. The patentees used directions from the examples of the patent, and where otherwise not instructed by the patent, standard chemical processes and handling were used.

In a glass vessel, 30 Kgms of reagent grade methanol and 0.90 Kgms of Lupasol WF were combined and stirred to produce a homogeneous solution. This was stock polymer solution (A).

To a glass lined reactor was charged 70 Kgms of reagent grade toluene. Thereafter, there was slowly charged, 9.0 Kgms of SIPERNAT 35 silica with stirring to aid dispersion. A further charge of 30 Kgms of toluene was made to the reactor slurry and the mix was continually stirred while heating the toluene to reflux, about 120° C.

The toluene in the mix was refluxed at approximately 120° C. for about 30 minutes with stirring to remove trace water. The need is to remove essentially all of the trace water from the system. The reactor is then cooled to 50° C. and then there is added 0.18 Kgms of deionized and deionized water and this was stirred for about 15 minutes. Over a period of one hour, there was slowly added 1.2 Kgms of silane (Dow Corning Z6040) to the reactor and this was stirred for an additional ½ hour and held at 50° C. taking care to avoid the fumes from the reaction which are methanol fumes. Thereafter, there was added 45 gms of toluene sulfonic acid and this was stirred for an additional 30 minutes.

The contents of the reactor were removed and placed into a bowl centrifuge to remove excess toluene. The filtrate was collected and re-added to the filter cake that had been created by the centrifugation, and it was repeated until the filtrate appeared clear. The filter cake was not allowed to dry out so that it would not crack or split.

Fresh toluene was added to the filter cake (60 Kgms) to rinse the filter cake. The filter cake was washed with 30 Kgms of reagent grade methanol and thereafter most of the methanol was removed, leaving enough so that the cake did not dry out. This step removed residual toluene. Thereafter, there was a final wash with 100 Kgms reagent grade methanol leaving a silica filter cake (B) that was dried to the point of cracking to enable easy removal from a belt centrifuge and this was added back to the reactor. All the waste solvents phases of toluene, methanol and mixtures were collected for waste disposal.

Thereafter there was added 45 Kgms reagent grade methanol and it was heated to 50° C. until there was a homogeneous slurry. The reactor was heated for an additional 2 hours.

Thereafter the dry filter cake was scraped off the drum and shoveled into a container for adding into the glass lined reactor. Forty-five Kgms reagent grade methanol were added to the glass lined reactor and heated to 50° C. over a 30 minute time before the dried filter cake was added to the reactor and stirred to redisperse the filter cake into the methanol. The condensation catalyst was added and the reactor contents were stirred for 1 hour to ensure homogeneous before the polymer stock solution A was added over a period of 15 minutes and it was heated to 50° C. until there was a homogeneous slurry. The reactor was heated for an additional two hours.

The contents of the reactor were removed and added to a bowl centrifuge to remove excess methanol. The filtrate was collected and re-added to the filter cake and this was repeated several times until a clear filtrate was obtained. The methanol was removed without cracking the filter cake.

Thereafter, 100 Kgms of reagent grade methanol was added and removed to wash the filter cake. There was then added 60 Kgms of pre-equilibrated 50% reagent grade ethanol (15 Kgms) and 50% deionized and deionized water (15 Kgms) and then this was removed while taking care not to allow cracking of the filter cake. Thereafter, deionized and deionized water (60 Kgms) was added and the material centrifuged to dryness with the filter cake cracking and it was easily removed by scraping. The finished dried filter cake was collected and packaged in a polymeric bag to protect it from drying out. All these waste solvents and water mixtures were collected and disposed as waste products. The resulting product was spray dried to a white powder.

EXAMPLE 11 Demonstration of Free Silane Coupling Agent Creating Cross-Linked Polymers This demonstration used the process of manufacture of this invention essentially in accordance with Example 2 using 5 micron silica wherein silica is reacted with a silane and the silane/silica product is reacted with polyethyleneimine to bind the polyethyleneimine to the siliceous substrate.

It is the contention of the inventors herein that by virtue of the reaction conditions of this invention, there is excess silane present in the reaction medium, that is, the silane that is not used to bind the polyethyleneimine to the siliceous substrate, and that this excess silane will have three functions, namely, (a) to cross link the polyethyleneimine primary imine groups within the molecules that are already bound to the siliceous substrate surface, (b) to cross link the polyethyleneimine imine groups with molecules in solution before they are bound to the surface, and (c) to cross link between those molecules already at the surface between the polyethyleneimine primary groups in neighboring molecules.

To a glass, open top vessel was added a predetermined amount of water, silica, a predetermined amount of silane, and a catalyst. After initial stirring to mix the ingredients, the reaction mass was allowed to stand still so that the silica that had grafted silane on it had time to settle to the bottom of the glass vessel. Excess, unreacted silane was present in the top liquid phase. This designed excess silane will have three functions; (a) to cross link the polyethyleneimine primary imine groups within the molecules that are already bound to the siliceous substrate surface, (b) to cross link the polyethyleneimine imine groups with molecules in solution before they are bound to the surface, and (c) to cross link between those molecules already at the surface between the polyethyleneimine primary groups in neighboring molecules.

The clear liquor as the top phase was decanted into a second open top glass vessel and then, the clear liquor was placed into a separate reactor vessel containing no silica, crosslinker or residual linker catalyst. Thereafter, a predetermined amount of a 25,000 molecular weight polymer (polyethyleneimine from BASF identified Supra) was added to the reactor vessel and the reaction was allowed to proceed.

FIG. 1 is a depiction of an actual gel permeation chromatography spectrogram showing a 25,000 molecular weight polyethyleneimine that is not grafted to any substrate. This depiction shows a single peak at 40 minutes elution defining the shape of the original polymer. The ordinate is RI voltage in mV and the ordinate is Time in minutes.

After the 25,000 PEI polymer was reacted in the top liquor phase, the reaction contents were analyzed, using the same conditions as was used to analyze the original polymer.

Figure 2:
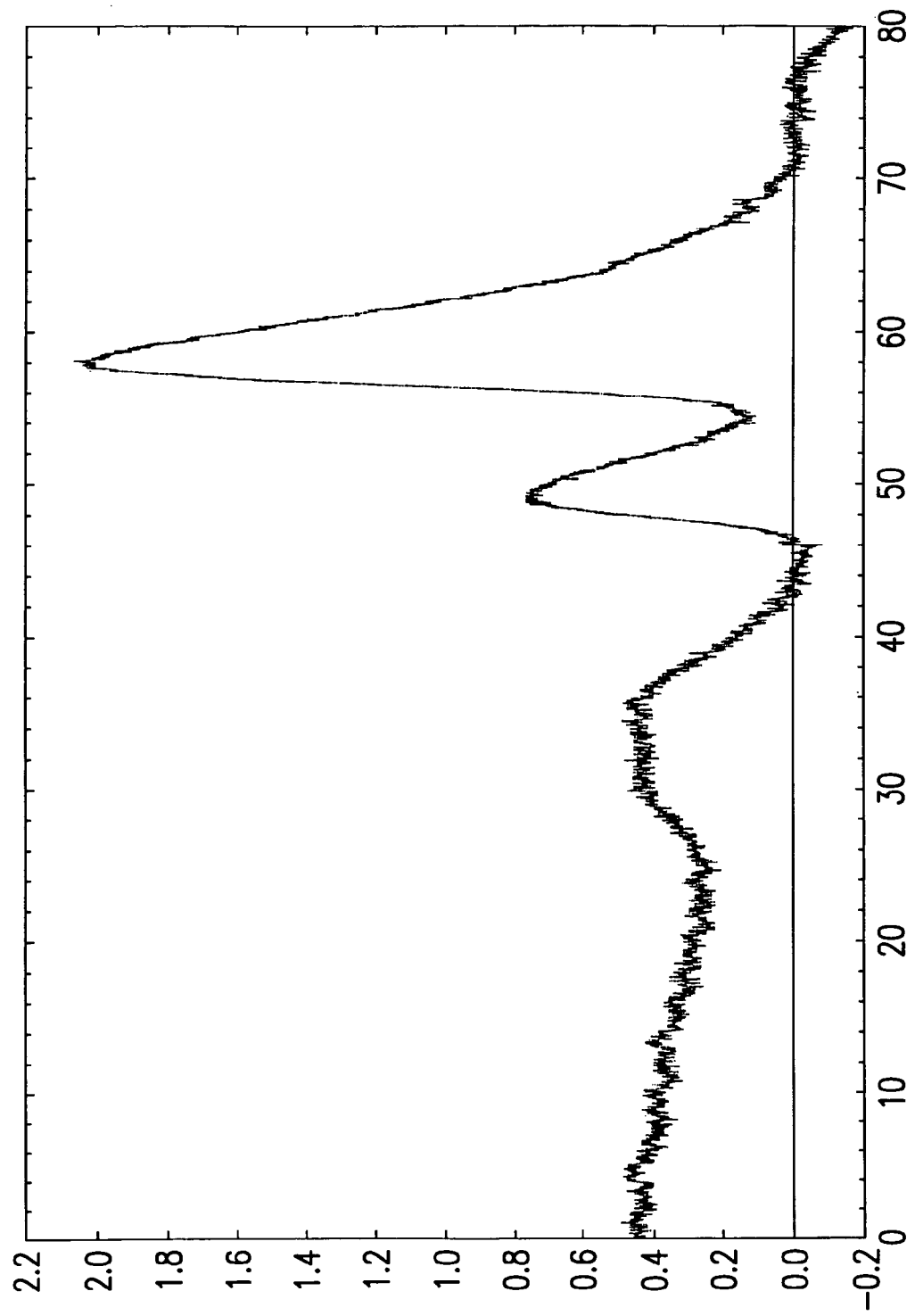
FIG. 2 is a GPC analysis of the polymer of FIG. 1 after (a) the silica has been added to water phase together with the selected hydrolysis catalyst and linker and then (b) the silica plus grafted linker has been removed leaving a clear liquor phase with a defined excess amount of unreacted linker, thereby showing the polymer is cross linked by unreacted linker in the inventive process herein.

FIG. 2 is a depiction of the actual gel permeation chromatography spectrogram showing that the single peak measured at 40 minutes elution, as shown in FIG. 1, changes to essentially three peaks at elution times of 35 minutes, 50 minutes and 60 minutes. This illustrates that with the extended gel permeation chromatography elutions, the polymer has been cross-linked by the residual silane and this cross linking effectively shrinks the polymer causing longer elution times. The 50 and 60 elution minutes reflect an agglomeration as well as self cross linking. It is likely that the 35 minutes elution illustrates polymer molecules that may not be cross linked. This process allows one to vary the cavity shapes and distributions of the polymer on the surface of the silica. The ordinate is RI Voltage in MV and the abscissa is Time in minutes.

Figure 3:
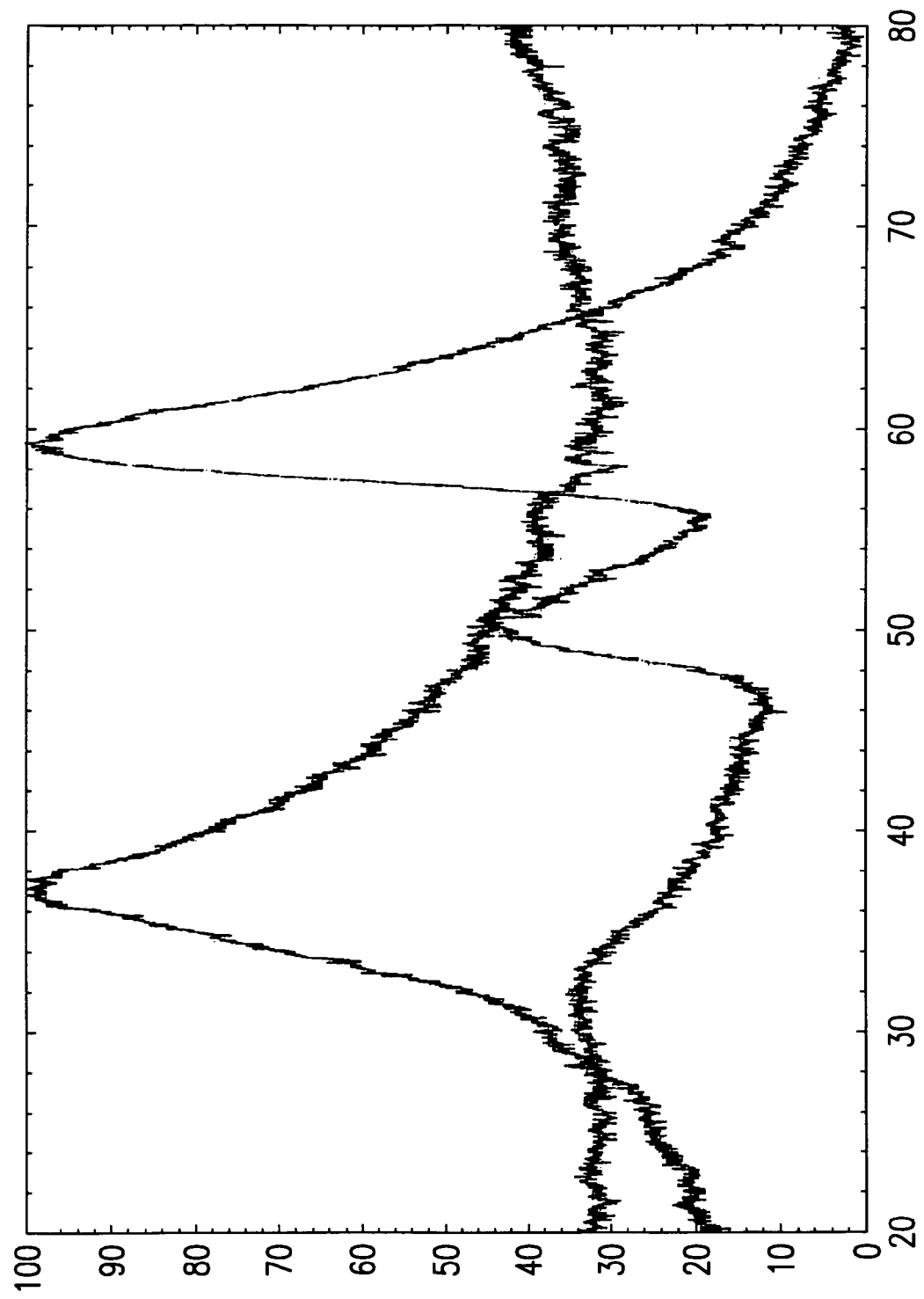
FIG. 3 is an overlay of FIG. 1 and FIG. 2 for comparison purposes.
Figure 4:
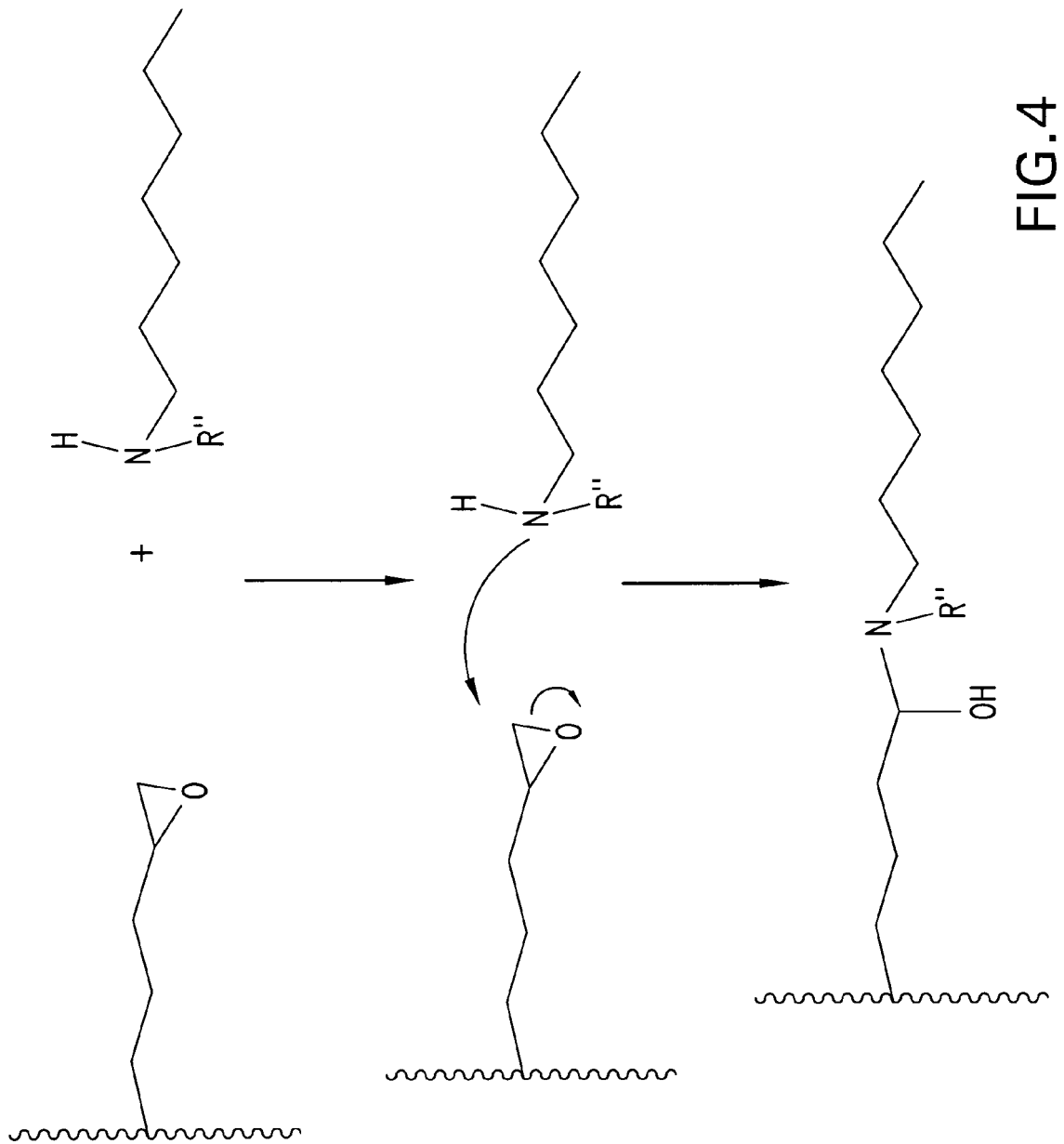
FIG. 4 is a schematic drawing of the chemistry of the instant invention wherein the PEI is reacted with the pendent silane that is attached to silica.
Figure 5:
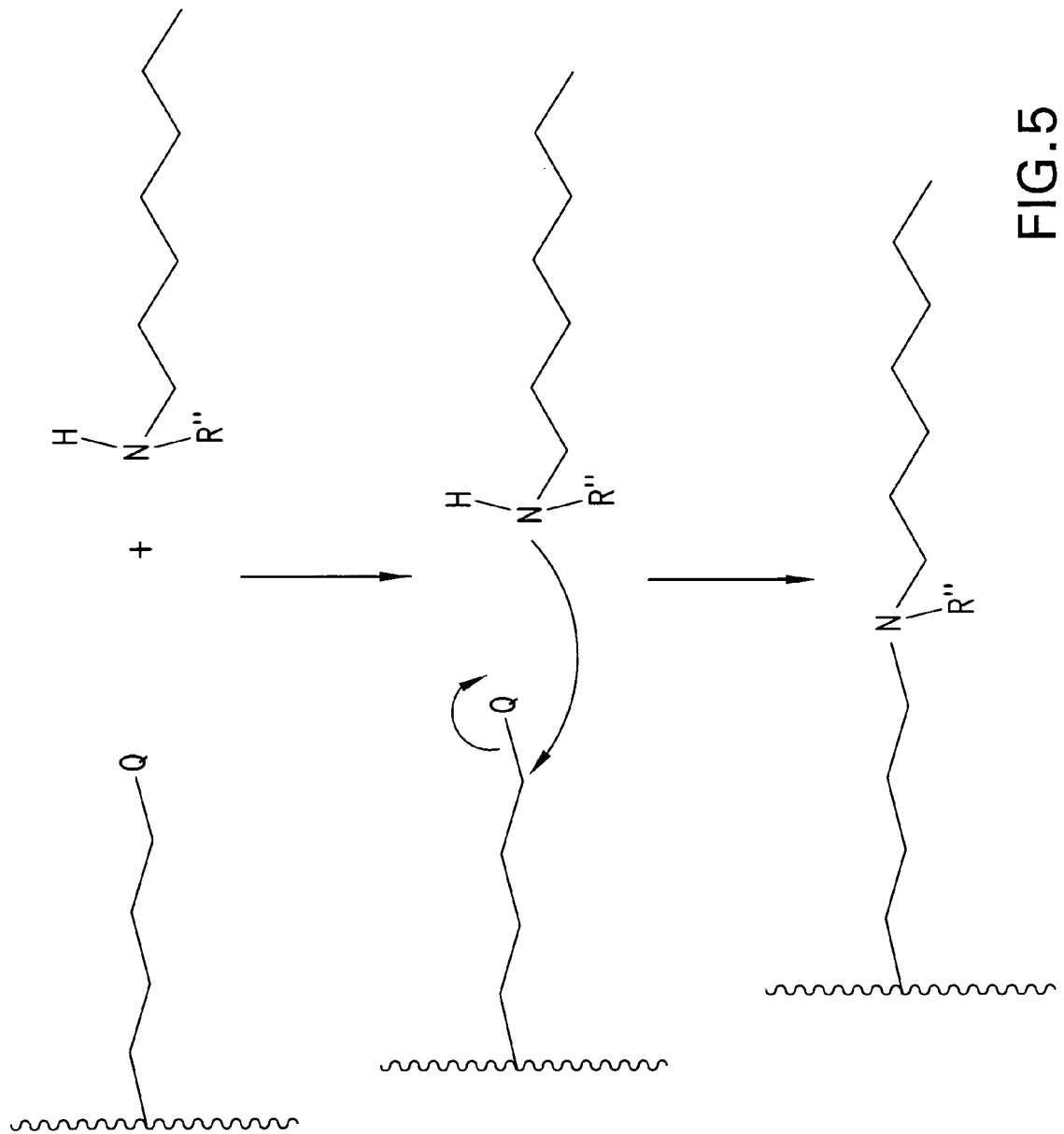
FIG. 5 is a schematic drawing of the chemistry of Rosenberg, U.S. Pat. No. 5,695,882 wherein Q is a leaving group.

For comparison purposes, FIG. 3 shows the depiction of FIG. 1 overlaying the depiction of FIG. 2 wherein the ordinate is relative amount in percent and the abscissa is Time in minutes.

In conclusion, this process allows for controlled cross-linking of the polymer both at the silica surface, creating a primary polymer layer, and perhaps more importantly, in the thicker multi-layers that are subsequently grafted to the primary polymer layer creating nanocavities of defined size and distribution.

EXAMPLE 12 Dye Transfer Inhibitor Studies

The procedure used herein is a modification of procedure ASTM D5548. In the ASTM procedure, a dyed cloth is used and the re-deposition of the bled dye from this dye cloth onto a white cloth is tested. In the modified method, a known concentration of the dye is added to the test liquor and its deposition onto a white fabric is measured.

The dye is used at about 10 ppm, the detergent concentration is at 0.1% and the detergent is typically anionic detergent, and in this case, WISK® at 1 gms/liter solution (Wisk is a Unilever household commercial detergent and was used without modification); the dye transfer inhibitor agent is typically about 10 to 100 ppm active; the standard test medium is tap water, and for hard water, there is a hard water test of 110 ppm equivalent hardness with Ca:Mg 3:1; the temperature is 100° F., and test cloths are typically cleaned, that is, washed cotton #400 in swatches sized to 3" by 4".

A Tergometer has six discrete chambers each for one set of operating conditions. Each chamber contains about 1 liter of the test liquor plus respective additives/swatch of cloths. The aqueous solutions are equilibrated to the selected temperature in the chambers before the swatches are immersed. We chose to immerse two or three swatches to each chamber and the washing process was performed for 10 minutes at a pre-set agitation rate of 100 cycles/minutes.

The swatches were removed and rinsed for 3 minutes in tap water. Excess water was squeezed out by hand and the swatches were allowed to dry in air prior to measuring their reflectance on a Hunter Colorimeter, (Reston, Va.). To minimize swatch variances, some 6 to 9 $\delta E$ readings were averaged from each swatch and were measured against an untreated white swatch as reference. Shown herein are the respective dye retention values for each test swatch as defined by the percentage reduction in the $\delta E$ values compared with the control watch for each product. The dye retention value=$(\delta E_{switch}) \times 100\%/(\delta E_{control})$ or $\delta E_{swatch}$ divided by $\delta E_{control}$ expressed as a %.

A control is normally run in each test wherein the liquor contains all of the components except polymer. The reflectance data from this control were used to judge the relative performance of the test polymers.

The dye represented infra with data from swatch tests using sample 10-005 having 10 weight % polymer on 5µ silica (Degussa/Sipernat 35) and sample 10-0P2 having 10 weight % polymer on 0.2µ silica (Cab-o-Sil-5) was the Direct Red 80. The same trends were observed with a selection of other dyes including Reactive Black 5, Acid Blue 113, Acid Red 151, Reactive Red 2 and Reactive Orange 16.

Figure 12:
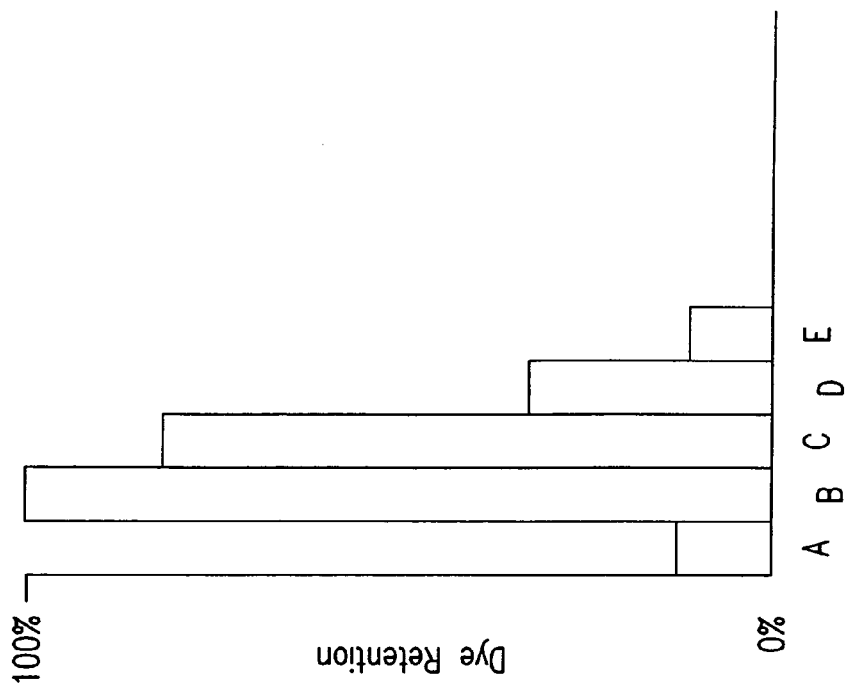
FIG. 12 is a histogram of the test results from Example 12, sample 10-0P2.
Figure 11:
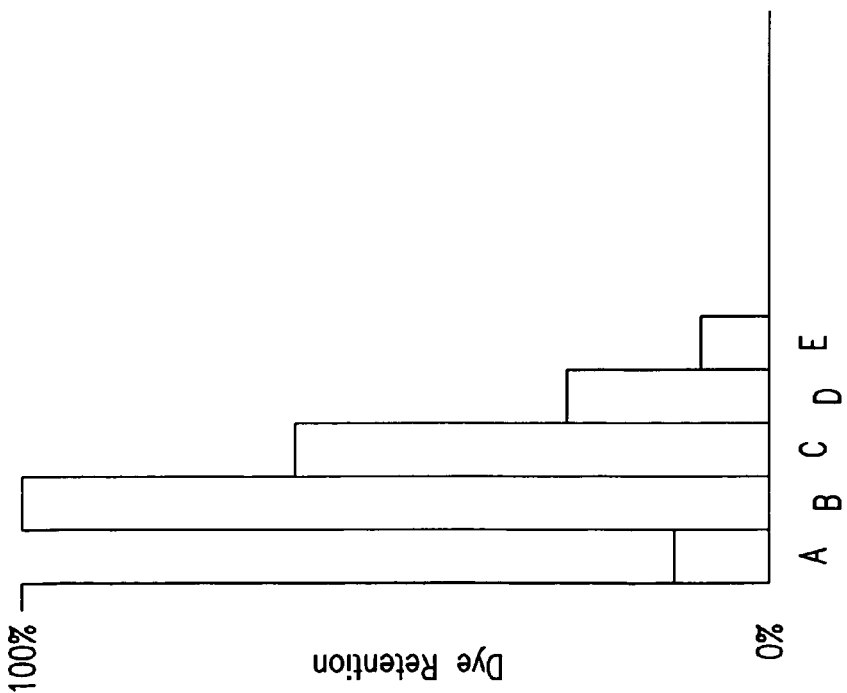
FIG. 11 is a histogram of the test results from Example 12, sample 10-003.

FIG. 11 is a histogram of the test results of the sample 10-005 wherein the ordinate is % dye retention and A-E are the samples, and FIG. 12 is a histogram of the test results of the sample 10-0P2 wherein the ordinates is % dye retention and A-E are the samples.

The commercial dye transfer inhibitor agent was a commercial brand comprising polyvinyl pyridine N-Oxide from Proctor and Gamble and used at 10 ppm active. The control was without the dye transfer inhibitor agent in 10 ppm Direct Red 80 dye. Both silicas were used without further purification. Neither product was optimized for these studies but showed relatively high performance across all the direct and acid dyes.

In each case: "A" was 10 ppm of the commercial brand polyvinyl pyridine N-Oxide dye Transfer inhibitor.
"B" was the control swatch.
"C" was 1 ppm of the sample.
"D" was 5 ppm of the sample.
"E" was 10 ppm of the sample.

EXAMPLE 13 Metal Cation Binding From Water in Packed Bed Columns

This example shows that metal cations in the form of salts in tap water taken in Princeton, N.J. (location of the laboratory) can be removed most efficiently when the aqueous solution is passed through a glass column packed with the inventive product. The efficacy of removal and capture of the metal cations can be related to the amount of polymer grafted to the surface of the silica. The water flux can also be related to the amount of polymer grafted to the surface of the silica which indirectly supports the concept of polymer cross linking and how the packed bed column can efficiently be used to remove toxic metals in an efficient manner. The propensity of the product to bind copper cation is a clear function of the thickness of the polymer grafted to the substrate surface.

Rhodia Tixosil 68 silica which is a nominal diameter 250 micron silica was treated with the polymer to varying degrees. The polymer was 25,000 Dalton molecular weight CAS#9002-98-6 polyethyleneimine. For comparison purposes, the samples had 1%, 2%, 5%, 10% and 20% polymer grafted to the surface of the silica from the same batch of Tixosil 68 precipitated silica.

The packed bed filtration columns were constructed as described Supra. Copper solutions, 100 ppm copper, were made up as copper sulphate in tap water in such volumes that they could be passed through the packed bed filtration columns for many hours with the same effective head of water pressure to maintain an even pressure flow through the bed. Samples were taken regularly from the base of the filtration column and analyzed by atomic spectrophotometer. The specific instrument used was a Varian Atomic Flame Absorption Spectrometer Model SpectrAA 240 FS. with sensitivities at the mg/L levels or ppm levels.

The elution samples were analyzed for metal content which, by extensive testing, determined that the levels were lower than ppb (lower limit of the spectrophotometer detection) until the breakthrough when the samples were shown by the method above to contain samples of respective metal cations of near the initial starting concentration of 100 ppm copper. No speciation determinations were made on any other samples.

The samples used in this study were analyzed to determine the amount of polymer grafted onto the silica using TGA using Simultaneous Thermal analyzer Model Netzsch STA 449C Jupiter, which combines Differential Thermal Analysis (DTA) with Thermogravimetry (TG) (Netzsch Instruments, Inc., Burlington, Mass.). The finished product was extensively washed in deionized water 5 or 6 times, allowed to settle under gravity and the free water phase decanted and then finally filtered through fine Whatman Grade #3 filter paper (Whatman Inc., Florham Park, N.J.) in order to collect the product and waste waters between each washing stage. The final collected product was then dried in a vacuum oven at 50° C. to achieve a constant weight before respective GPC analysis. The amount of analyzed polymer was within ±2 of expected polymer layer and well within the experimental accuracy of the analysis program.

Figure 13:
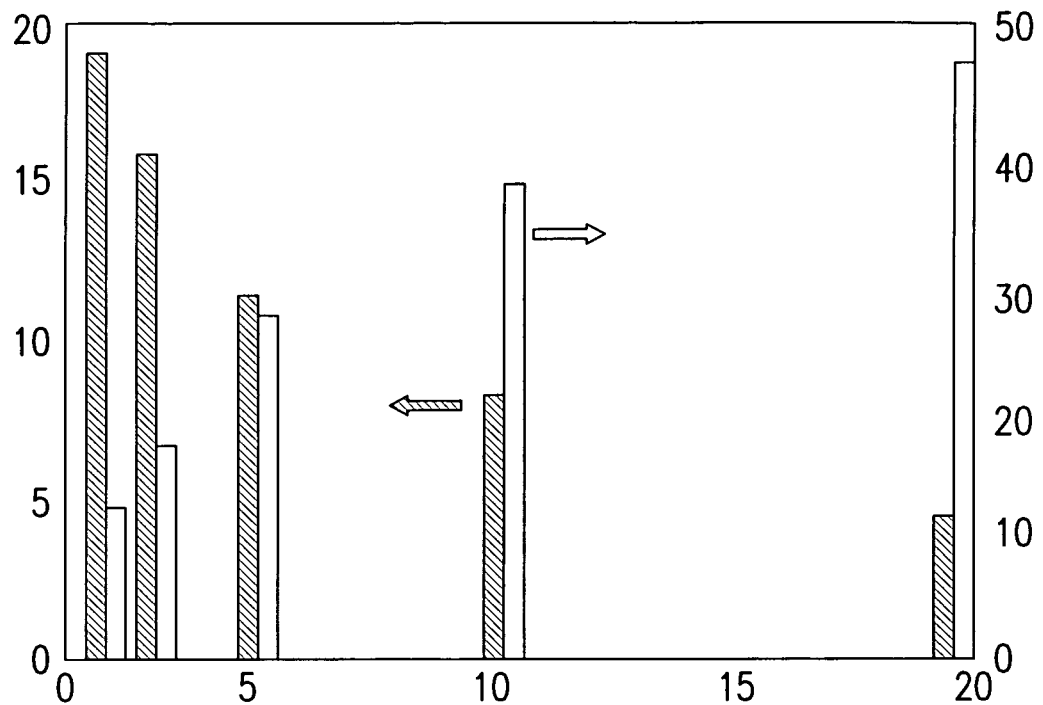
FIG. 13 is a histogram of comparative date from Example 15.

The binding and retention of the copper cation from aqueous solutions of 100 pm copper, as a copper sulphate solution in tap water is shown in FIG. 13 wherein the left hand ordinate is % copper retained/weight polymer; right ordinate is water flux in # column void volumes, and the abscissa is the % polymer grafted to silica by weight.

The binding and retention of the copper cation from aqueous solutions of 100 ppm copper, as a copper sulphate solution in tap water is shown in FIG. 13 wherein the left hand ordinate is % copper retained/weight polymer; right ordinate is water flux in # column void volumes, and the abscissa is the % polymer grafted to silica by weight.

It is clear from the data that when the grafted polymer was increased from 1% by weight silica to 20% by weight of silica, the total amount of copper bound within the polymer matrices differ as indeed does the volume of flow before breakthrough occurs. It is to be noted that the weight of copper bound with the polymer, when expressed as "% bound by weight of polymer grafted to the silica", decreased as the total weight of polymer grafted to the silica increased. Indeed, the amount of copper bound at breakthrough decreased from 19.2 gms Cu per gm grafted polymer with only 1% grafted polymer to 4.8 gms Cu per gm polymer with 20% grafted polymer. By contrast, the flux of copper sulphate through the respective packed bed columns increased from 10.3 void volumes to breakthrough with 1% grafted polymer up to 48.0 void volumes when flowing through packed bed with silica and 20% grafted polymer.

The grafting of the increasing amounts of polymer creates a thicker polymer matrix which is cross linked thereby creating nano cavities in which the metal cations are bound. These nano cavities are the seeds for metal cation retention and the more there are, the higher the propensity for metal capture. However, when the polymer matrix becomes too thick, then the metals bound in the outer polymer nano cavities will act as a barrier for other inner layers to be populated with cations. Consequently, the total metal bound by weight of total polymer grafted will decline. However, the thicker polymer matrix will allow space between the silica particles thereby allowing small but measurable greater space for water flux to occur through the packed bed. Because there is higher amount of polymer grafted, although it will not all be playing an efficient role in binding copper, this will allow greater void volumes of water flux thereby allowing greater volumes of water to be treated.

EXAMPLE 14 Agglomerate Dye Removal Studies

This agglomerative test uses acid and reactive dyes which are known in the industry and by those skilled in the art to be difficult to remove from solution and fabrics. The potency to remove dyes from fabric swatches has been shown above and we concentrate on demonstrating the potency to remove dyes from solution in this study. This would simulate the removal of dyes from fabric dye waste water streams.

The dyes used included Reactive Black 5, Reactive Orange 16, Direct Red 81, Acid Blue 113, and Pylaklor Fast Green S 567. Respective dyes stock solutions were made at 110 ppm in deionized water. The water phase was once deionized water.

The product selected for this study was a 10% polyethyleneimine bound to 5 micron diameter silica supplied by Degussa Corporation and sold as Sipernat 350. A single stock solution at 1100 ppm was made in deionized water. FIGS. 15 to 18 are shown as dyes at 10 ppm and 10 weight percent polyethyleneimine polymer grafted to 5 micron silica at 100 ppm.

For the tests, two samples were made as infra for each test dye. An aliquot of the product with polymer grated to silica was added to one sample with the other sample being used as a standard. Thirty mls of the respective dye solution is added to each of the two 33 ml capacity centrifuge tubes along with either 3 mls deionized water or 3 mls of the stock solution, respectively.

The two cells were then simultaneously shaken by hand to effect mixing of the twin tube contents for 20 seconds. The twin tubes are then added to a bench centrifuge and spun for 2 minutes at 3000 rpm to clarify the test cells of products. When completed, the centrifuge was stopped without severe braking in order not to mix the separated polymer phase from the base of the tube. Then 10 mls of the respective upper liquor phases were withdrawn and sealed for analysis using a standard twin beam UV/VIS spectrophotometer.

Figure 15:
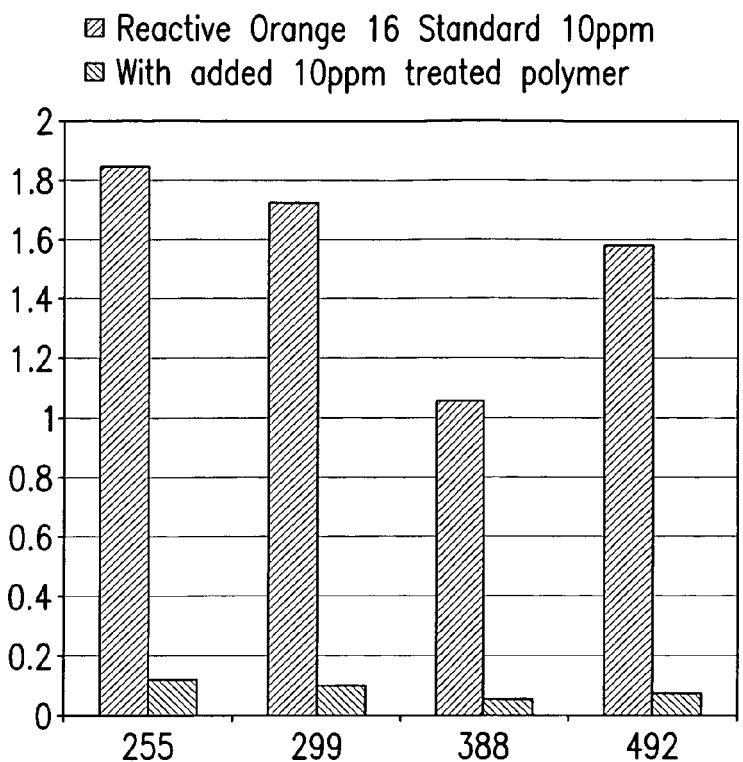
FIG. 15 is a histogram of the test results from Example 14, Reactive Orange 16.
Figure 16:
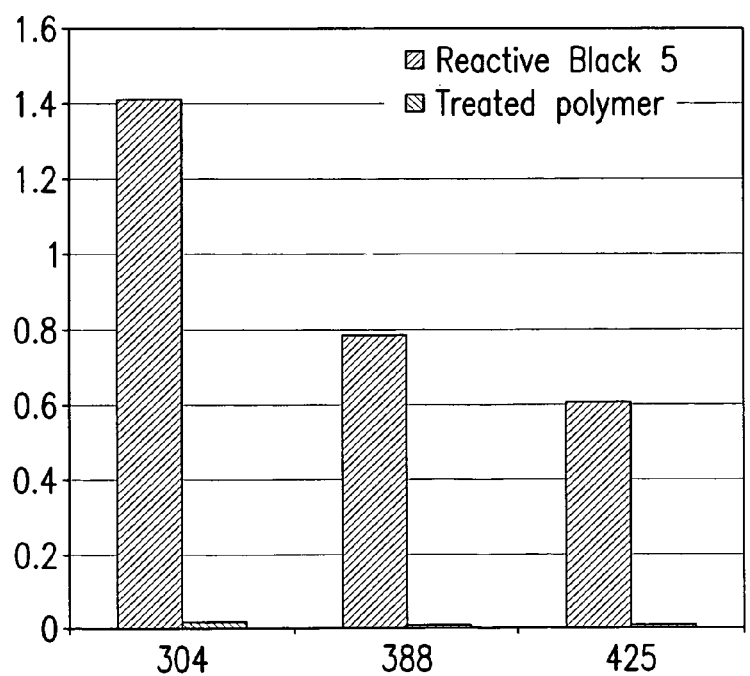
FIG. 16 is a histogram of the test results from Example 14, Reactive Black 5.
Figure 17:
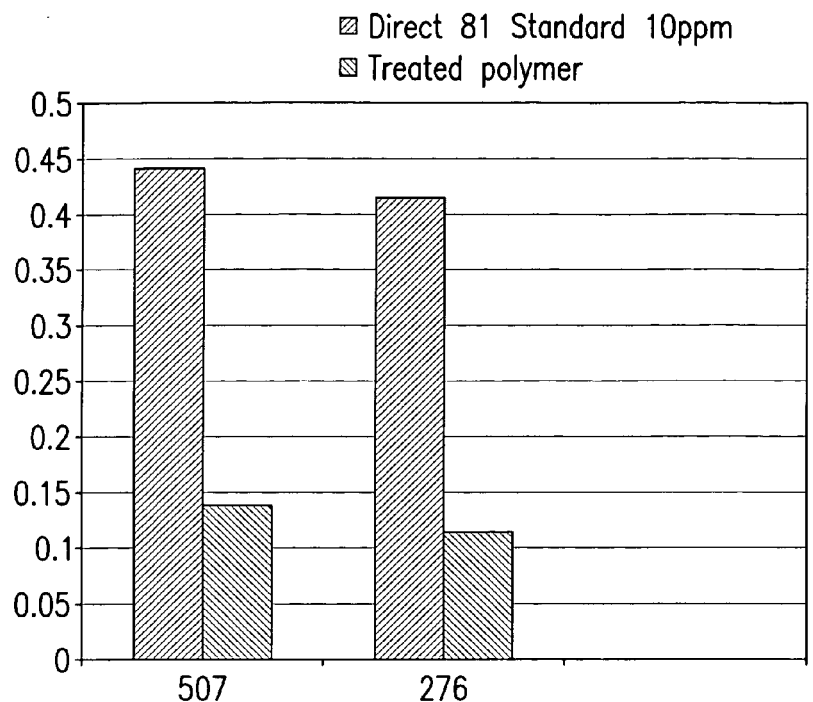
FIG. 17 is a histogram of the test results from Example 14, for Direct Red 81.
Figure 18:
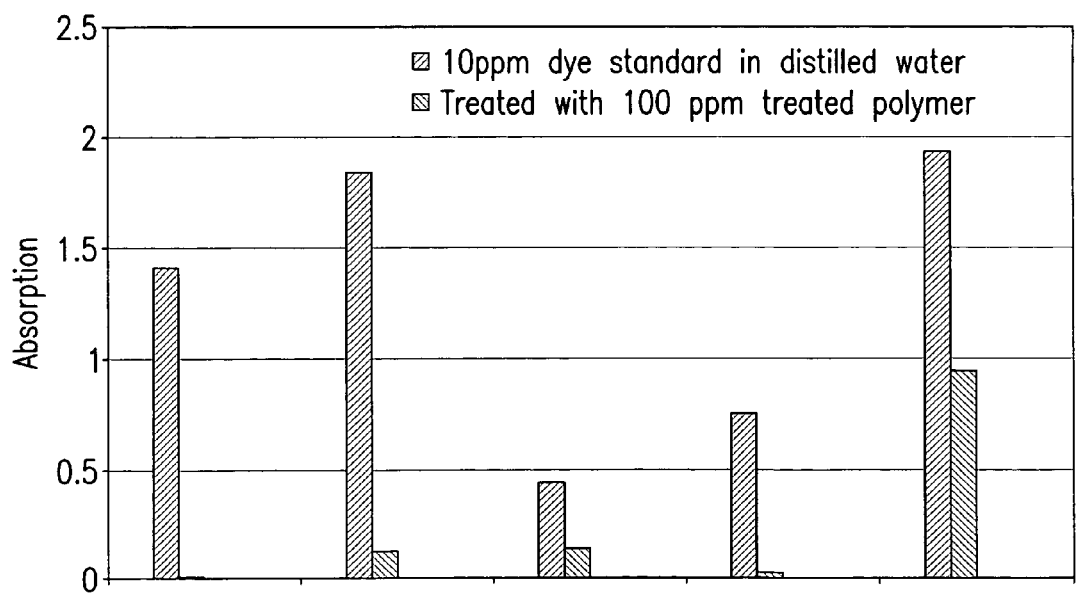
FIG. 18 is a histogram of the test results from Example 14, comparative data.

Using the 5 selected dyes, the analysis involved some 10 samples consisting of 5 each containing 100 ppm dye as standard and 5 with the test 100 ppm product. The results are shown in histogram form in FIGS. 15 to 18 for the selected dyes Reactive Orange 16, Reactive Black 5, Direct Red 81, across a range of wavelengths and then as a comparative histogram for the above dyes together with other difficult to remove dyes such as Acid Blue 13 and Pylaklor Fast Green S-567. FIG. 15 shows the results for Reactive Orange 16, FIG. 16 for Reactive Black 5, FIG. 17 for Direct Red 81, wherein in each Figure, the ordinate is absorbance and the abscissa is the wavelength in $cm^{-1}$ and FIG. 18 shows the comparative data.

It can be concluded from the data that each of the sample dyes, when added to deionized water at the 10 ppm level, can be significantly removed by the addition, shaking and sedimentation by centrifuging of the selected agglomerating product. The absorbance data show clearly that each dye can be significantly reduced. The results above show the selective removal as measured across a wide range of colored wavelengths for the dyes. As shown in the comparative removal FIG. 18, the Pylaklor Fast Green S-567 is also reduced although some wavelengths are reduced more than others such that the green spectrum becomes more of a yellow pigment.

The agglomerate removal using product that is 10% polyethyleneimine grafted onto 5 micron silica is also confirmed when the dye solution is passed through a packed bed column of the product that is 10% polyethyleneimine on 250 micron silica as described in the metal filtration studies. The solution dye is complexed with the polymer grafted to the surface of the silica particle and can be seen as a concentrated dye bound tightly to the upper limits of the pack bed column with clean water, devoid of any detectable dye, passing through the column bed. Consequently, the dye can be removed by either agglomeration mode or packed bed filtration mode.

EXAMPLE 15 Competitive Binding and Displacement of Metal Cations

The metal cations that can be captured by the inventive media include, for example, copper, lead, iron, silver and mercury. FIG. 14 shows the displacement factors associated with the various metals when using a polymer of this invention wherein vvv means easier displacement than vv and in turn easier than v; xxx means less likely to displace than xx, and in turn less than x.

A packed bed column was prepared as set forth above. A 100 ppm primary metal cation concentration as a metal sulphate solution at roughly pH 6 was passed through a previously prepared packed bed column consisting of a product having 10 weight percent polymer bound to Rhodia's 250 micron Tixosil 68 silica. The flowing elution was allowed to continue until the column showed solution breakthrough, in other words, the binding cavities in the polymer matrix are now fully saturated with the primary metal. Tap water was then passed through the column for at least 10 column water void volumes to demonstrate that no primary metals cations were displaced and were bound tightly. The secondary metal cation solution was then passed down the column and the eluate collected at the bottom of the packed bed and saturated with the primary metal cation column. This eluate was analyzed for the primary and the secondary metal cations to determine the ability of the metal ions to displace its partners. The resulting FIG. 14 shows that the propensity of the primary metal cations to displace the secondary metal cations, in the inventive system that was Cu≈Hg>Fe>Pb>Ag.

This series is similar to the charge densities of the metal cations and can be reflected by the capacity of the nano cavities within the cross linked polymer matrix to complex with, and to bind, a blend of similar metal cations. By extending this principle, the section and propensity of metal and non-metal cations can be predicted for binding and removal.

What is claimed is:

1. A process for preparing a crosslinked polymer that is chemically bonded to the surface of a siliceous substrate, said process consisting essentially of:
   (I) heating a predetermined amount of water in a reaction vessel with stirring;
   (II) adding a predetermined amount of a hydrolysis catalyst that is an organic acid, said organic acid having from 1 to 7 carbon atoms:
   (III) thereafter, adding a predetermined amount of a siliceous substrate having reactive silanols;
   (IV) thereafter, adding a predetermined amount of incipient silane to provide a silane linking material, said silane being an alkoxy-functional silane having the general formula (RO)$_3$ SiQX wherein R is a hydrocarbon group having from 1 to 6 carbon atoms, Q is a hydrocarbon group having from 0 to 6 carbon atoms, X is a functional group selected from the group consisting of epoxy, halogen, methacrylate, vinyl, amine, allyl, phosphonate, styrlamine, and sulfide;
   (V) thereafter, adding a predetermined amount of silanol condensation catalyst;
   (VI) thereafter, adding a predetermined amount of polymer, said polymer being selected from the group consisting of (i) a water soluble polymer,
   (ii) a water soluble copolymer,
   (iii) an alcohol soluble polymer,
   (iv) an alcohol soluble copolymer, and
   (v) combinations of (i) to (iv),
   (VII) thereafter, additionally stirring the combination of the components of (I) to (VI) for a period of time of 15 hours or less at a temperature of 100° C. or less; wherein the incipient silane is present in the amount of 0.1 to 25 weight percent based on the amount of siliceous substrate and wherein the incipient silane is present in an excess with regard to the total amount of reactive silanol groups of the siliceous substrate.

2. A process as claimed in claim 1 wherein the organic acid is acetic acid.

3. A process as claimed in claim 1 wherein the amount of organic acid present in the reaction vessel provides a pH of 4.5 or less.

4. A process as claimed in claim 1 wherein the condensation catalyst is a water soluble alkylbenzylsulfonic acid.

5. A process as claimed in claim 4 wherein the condensation catalyst is toluene sulfonic acid.

6. A process as claimed in claim 1 wherein the condensation catalyst is present in the reaction vessel is 0.05 to 5.0 weight percent based on the weight of the siliceous substrate.

7. A process as claimed in claim 1 wherein the process time does not exceed twelve hours.

8. A process as claimed in claim 1 wherein the silane linking material is derived from the silane

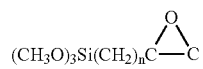

wherein n has a value of 1 to 3.

9. A process as claimed in claim 1 wherein the surface area of the siliceous substrate is about 3 to 300 m$^2$/gram.

10. A process as claimed in claim 1 wherein the polymer is polyethylene imine.

11. A process as claimed in claim 1 wherein the polymer has a molecular weight in the range of 1000 to 200,000 Daltons.

12. A process as claimed in claim 1 wherein the weight of the polymer on the siliceous substrate is in the range of about 1 to 20 weight percent based on the total weight of the polymer and the siliceous substrate.

13. A process as claimed in claim 1 wherein the weight of the polymer on the siliceous substrate is in the range of about 5 to 15 weight percent based on the total weight of the polymer and the siliceous substrate.

14. A process as claimed in claim 1 wherein the weight of the polymer on the siliceous substrate is in the range of about 7 to 12 weight percent based on the total weight of the polymer and the siliceous substrate.

* * * * *